(12) United States Patent
Kawasaki

(10) Patent No.: US 11,564,704 B2
(45) Date of Patent: Jan. 31, 2023

(54) ENERGY TREATMENT SYSTEM

(71) Applicant: OLYMPUS CORPORATION, Hachioji (JP)

(72) Inventor: Minoru Kawasaki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 957 days.

(21) Appl. No.: 16/389,318

(22) Filed: Apr. 19, 2019

(65) Prior Publication Data

US 2019/0239920 A1 Aug. 8, 2019

Related U.S. Application Data

(63) Continuation of application No. PCT/JP2016/080981, filed on Oct. 19, 2016.

(51) Int. Cl.
*A61B 17/32* (2006.01)
*A61B 18/12* (2006.01)
*A61B 17/00* (2006.01)

(52) U.S. Cl.
CPC ...... *A61B 17/320092* (2013.01); *A61B 18/12* (2013.01); *A61B 2017/0003* (2013.01);
(Continued)

(58) Field of Classification Search
CPC ............ A61B 17/320092; A61B 18/12; A61B 2017/0003; A61B 2017/00123; A61B 2017/320094; A61B 2017/320082
See application file for complete search history.

(56) References Cited

U.S. PATENT DOCUMENTS

2010/0168742 A1 7/2010 Shibata
2014/0088464 A1* 3/2014 Kitayama ...... A61B 17/320092
601/2
(Continued)

FOREIGN PATENT DOCUMENTS

CN 105916459 A 8/2016
JP 2009-247887 A 10/2009
(Continued)

OTHER PUBLICATIONS

May 12, 2020 Office Action issued in Japanese Patent Application No. 2018-546091.
(Continued)

*Primary Examiner* — Toan M Le
(74) *Attorney, Agent, or Firm* — Oliff PLC

(57) ABSTRACT

In an energy treatment system, a processor temporally detects an electrical property value of an ultrasonic transducer, holds a temporary peak value of the electrical property value, detects an impedance value between the probe electrode and the jaw electrode, and compares the electrical property value and the temporary peak value to determine whether a predetermined condition is satisfied, and whether the impedance value exceeds a predetermined threshold. In response to determining that the electric property value satisfies the predetermined condition and the impedance value is larger than the predetermined threshold, the processor performs at least one of: (i) stopping and (ii) decreasing output from the first power supply, and notifying the determination result.

21 Claims, 16 Drawing Sheets

(52) U.S. Cl.
CPC .............. *A61B 2017/00123* (2013.01); *A61B 2017/320082* (2017.08); *A61B 2017/320094* (2017.08); *A61B 2017/320095* (2017.08)

(56) References Cited

U.S. PATENT DOCUMENTS

2016/0256190 A1   9/2016   Tsubuku
2016/0287317 A1   10/2016  Tsubuku et al.

FOREIGN PATENT DOCUMENTS

| JP | 2010-005370 A | 1/2010 |
| WO | 2010/076869 A1 | 7/2010 |
| WO | 2015/122307 A1 | 8/2015 |
| WO | 2015/122309 A1 | 8/2015 |

OTHER PUBLICATIONS

Feb. 1, 2021 Office Action issued in Chinese Patent Application No. 201680090244.0.
Jan. 24, 2017 International Search Report issued in International Patent Application No. PCT/JP2016/080981.
Jan. 24, 2017 Written Opinion issued in International Patent Application No. PCT/JP2016/080981.
May 2, 2019 English Translation of IPRP and Written Opinion issued in International Application No. PCT/JP2016/080981.
Sep. 7, 2021 Office Action issued in Japanese Patent Application No. 2020-167135.

\* cited by examiner

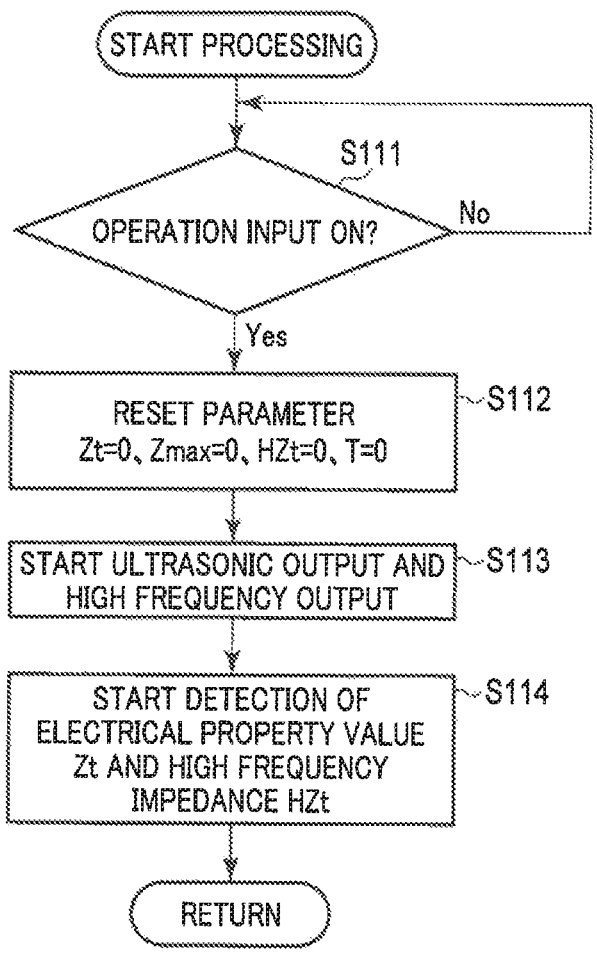
F I G. 5

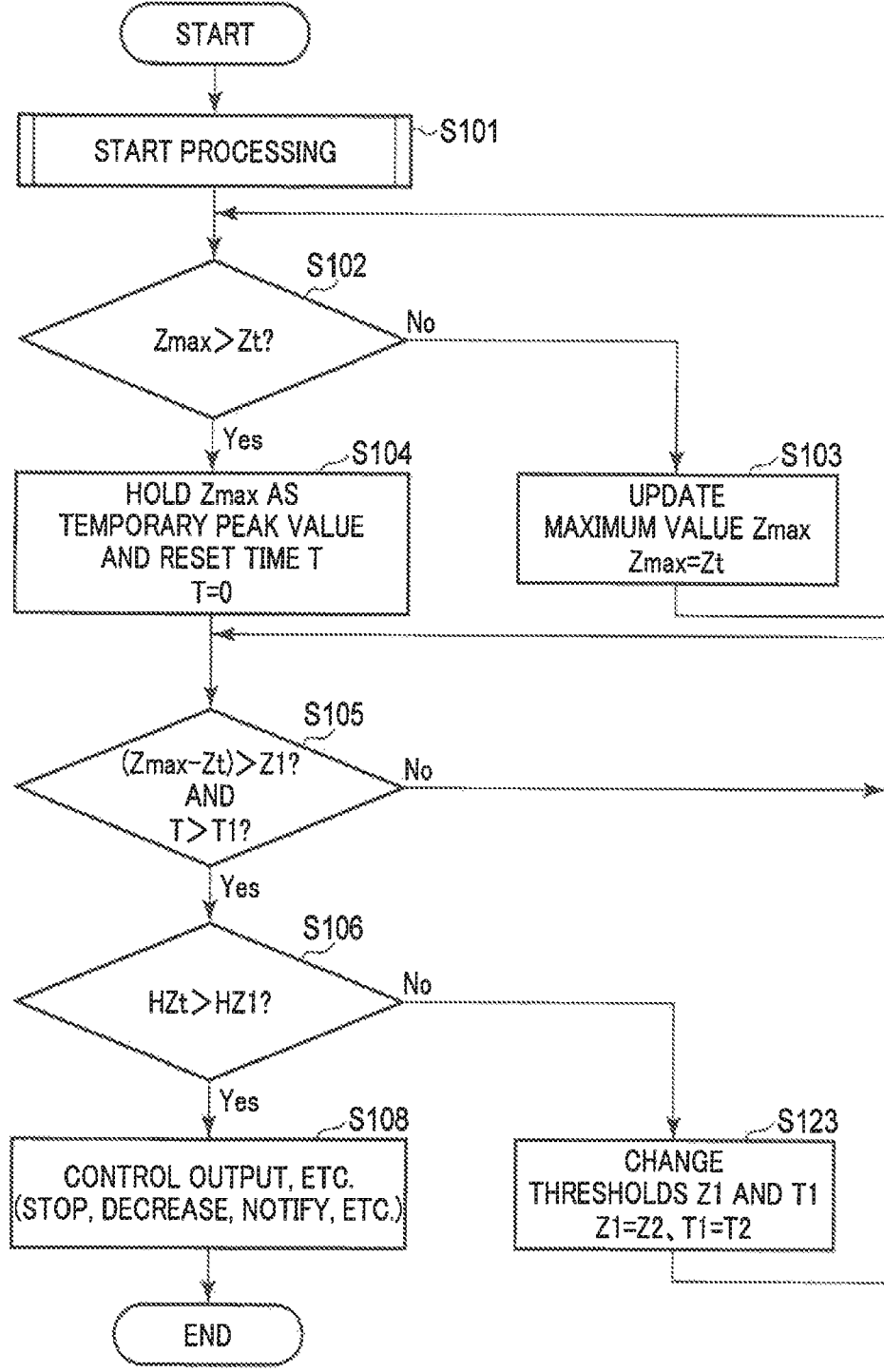
F I G. 7

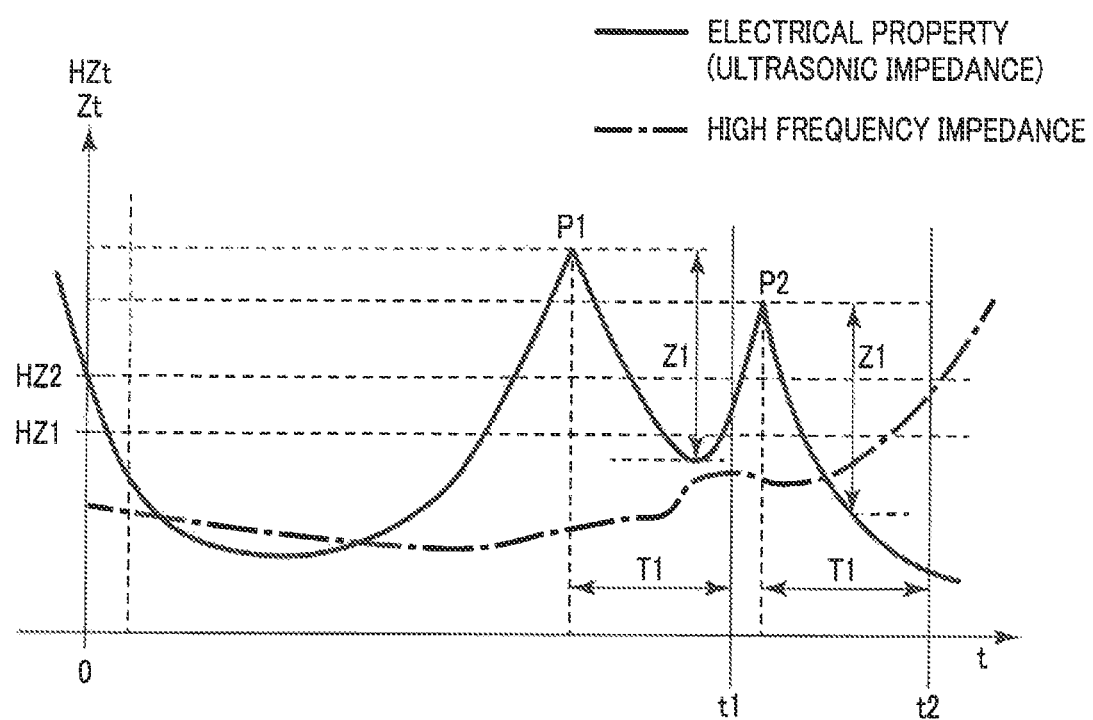
F I G. 13

ENERGY TREATMENT SYSTEM

CROSS-REFERENCE TO RELATED APPLICATION

This application is a Continuation Application of PCT Application No. PCT/JP2016/080981, filed Oct. 19, 2016, the entire contents of which are incorporated herein by references.

BACKGROUND

1. Field of the Invention

The present exemplary embodiments relate to an energy treatment system that treats a treatment target by using ultrasonic vibration.

2. Description of the Related Art

There is known an energy treatment system that has a treatment apparatus performing treatment such as coagulation or incision of a treatment target by using ultrasonic vibration energy or a treatment apparatus performing treatment such as coagulation or incision of a treatment target by combination of treatment using ultrasonic vibration energy and treatment using high frequency electric energy.

For example, in a prior treatment system treats body tissue by using ultrasonic vibration energy and high frequency electric energy in combination. In this system, the output of an ultrasonic output module is adjusted based on the impedance of the body tissue calculated from high frequency current and high frequency voltage output from the high frequency output module.

In another example, a treatment system treats body tissue by using ultrasonic vibration energy and high frequency energy in combination. In this system, an ultrasonic impedance calculation section calculates an ultrasonic impedance value, and a control section controls the output of high frequency energy by using the calculated value.

SUMMARY

According to an exemplary embodiment, an energy treatment system is provided. The energy treatment system includes a first power supply, a second power supply, an ultrasonic transducer configured to generate ultrasonic vibration by electric power supplied from the first power supply, a first gripping piece to which the ultrasonic vibration generated by the ultrasonic transducer is transferred and which is configured to perform treatment on a treatment target using the ultrasonic vibration, the first gripping piece having a probe electrode through which a current flows by electric power supplied from the second power supply, a second gripping piece which has a jaw electrode which is supplied with electric power from the second power supply and is opened and closed to the first gripping piece so as to grip a treatment target together with the first gripping piece, and circuitry configured to temporally detect an electrical property value of the ultrasonic transducer, hold a temporary peak value of the electrical property value, detect an impedance value between the probe electrode and the jaw electrode, compare the electrical property value and the temporary peak value to determine whether a predetermined condition is satisfied, and whether the impedance value exceeds a predetermined threshold, and when it is determined that the electric property value satisfies the predetermined condition and the impedance value is larger than the predetermined threshold, perform at least one of stopping or decreasing output from the first power supply and notifying the determination result.

Advantages will be set forth in the description which follows, and in part will be obvious from the description, or may be learned by practice of the invention.

BRIEF DESCRIPTION OF THE SEVERAL VIEWS OF THE DRAWINGS

The accompanying drawings, which are incorporated in and constitute a part of the specification, illustrate exemplary embodiments, and together with the general description given above and the detailed description of the exemplary embodiments given below, serve to explain the principles of the exemplary embodiments.

FIG. 5 is a diagram illustrating an example of start processing of the flow of treatment.

FIG. 7 is a diagram illustrating an example of a flow of treatment of an energy treatment system according to a second modification of the first exemplary embodiment.

FIG. 13 is a diagram illustrating an example of temporal changes in electrical property and high frequency impedance of an ultrasonic transducer during treatment.

DETAILED DESCRIPTION

First Exemplary Embodiment

An energy treatment system 1 (hereinafter referred to as a treatment system 1) according to a first exemplary embodiment will be described with reference to FIGS. 1 to 12.

Figure 1:
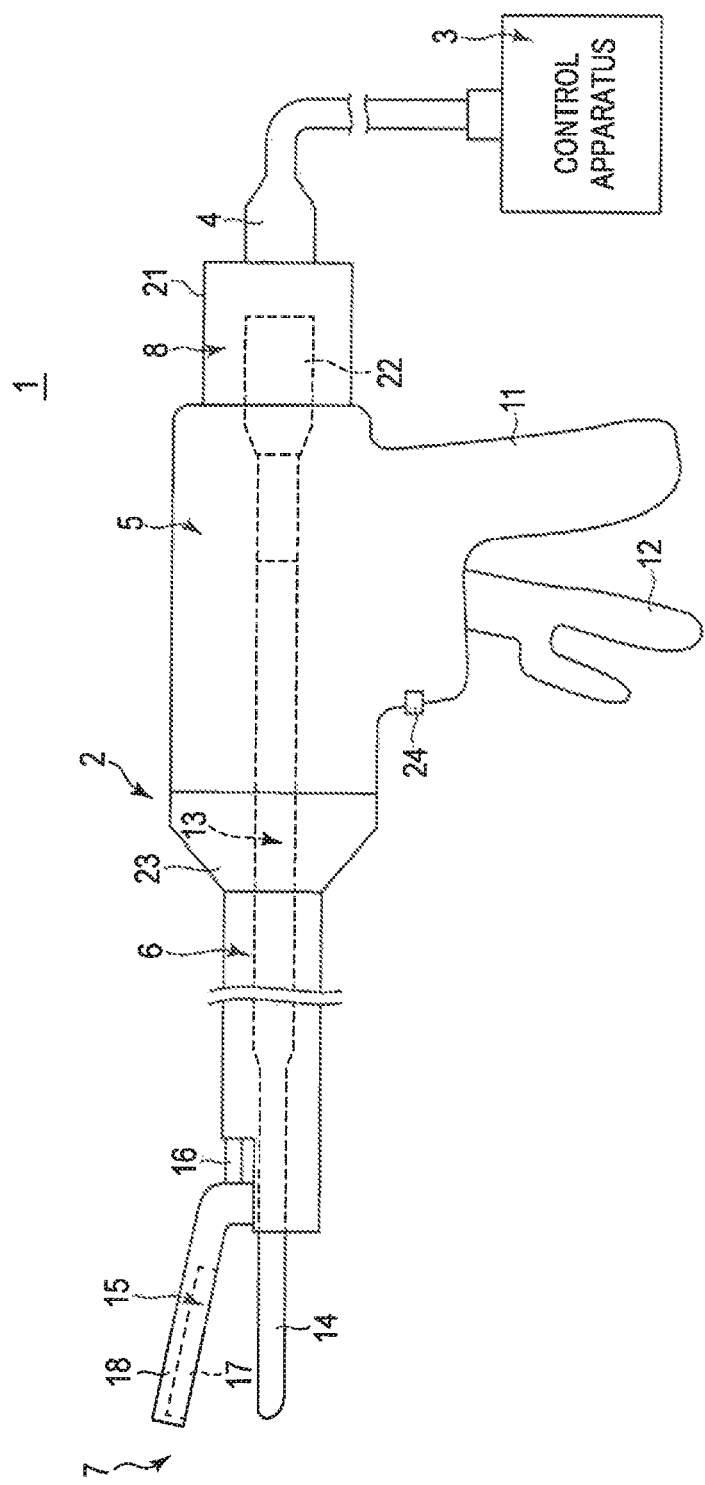
FIG. 1 is a schematic diagram illustrating an example of an energy treatment system according to a first exemplary embodiment.

FIG. 1 is a schematic diagram illustrating a treatment system 1. The treatment system 1 has a treatment apparatus 2 and a control apparatus 3. The treatment system 1 is configured to perform treatment such as coagulation or incision of a treatment target (for example, body tissue) by using ultrasonic vibration and high frequency current in combination. The treatment apparatus 2 is a handpiece to be gripped by an operator and is a surgical energy device capable of simultaneously outputting ultrasonic vibration energy and bipolar high frequency energy (electric energy generated by flowing a high frequency current through a bipolar electrode). The treatment apparatus 2 is attachably and detachably connected to the control apparatus 3 by a cable 4.

The treatment apparatus 2 has a housing 5, a sheath 6 distally coupled to the housing 5, an end effector 7 (a first gripping piece 14 and a second gripping piece 15 described later) provided at the distal end portion of the sheath 6, and a transducer unit 8 proximally coupled to the housing 5. The housing 5 is provided with a fixed handle 11. The housing 5 also has a movable handle 12 attached in a rotatable manner. When the movable handle 12 rotates with respect to the housing 5, the movable handle 12 is opened or closed to the fixed handle 11.

In the treatment apparatus 2, a probe 13 extends in a direction toward the distal end passing from the inside of the housing 5 to the inside of the sheath 6. The probe 13 is made from a material with high vibration transmissibility such as 64 titanium (Ti-6Al-4V). The distal end portion of the probe 13 constitutes a first gripping piece 14. The probe 13 is inserted into the sheath 6 such that the first gripping piece 14 protrudes from the distal end of the sheath 6. The first gripping piece 14 functions as a probe treatment section that transfers the ultrasonic vibration of the ultrasonic transducer 22 described later and performs treatment by the ultrasonic vibration on the treatment target. The first gripping piece 14 includes a probe electrode for applying high frequency energy to the treatment target together with the second gripping piece 15, which is further described later.

The second gripping piece (jaw) 15 is attached to the distal end portion of the sheath 6 in a rotatable manner. A part of the second gripping piece 15 functions as a jaw electrode for applying high frequency energy to the treatment target together with the first gripping piece 14. Therefore, the first gripping piece 14 and the second gripping piece 15 function as a pair of electrodes (probe electrode and jaw electrode).

In the inside of the sheath 6, a movable member 16 extends in a direction from the proximal end to the distal end. The distal end of the movable member 16 is connected to the second gripping piece 15. Although not illustrated, the proximal end portion of the movable member 16 is coupled to the movable handle 12 in the inside of the housing 5. When the movable handle 12 is opened or closed relative to the fixed handle 11, the movable member 16 moves in a direction towards the proximal end or the distal end. Accordingly, the second gripping piece 15 rotates relative to the sheath 6, and the second gripping piece 15 is opened or closed relative to the first gripping piece 14 (i.e., the second gripping piece 15 rotates towards or away from the first gripping piece 14).

The second gripping piece 15 has a pad 17 and a holder member 18 to which the pad 17 is attached. The pad 17 is made from a fluorine resin such as polytetrafluoroethylene (PTFE) and has electrical insulation properties. While there is no space between the first gripping piece 14 and the second gripping piece 15, the pad 17 is in abutment with the first gripping piece 14. While the pad 17 is in abutment with the first gripping piece 14, no other than the pad 17 in the second gripping piece 15 are in abutment with the first gripping piece 14. That is, even when there is no space between the first gripping piece 14 and the second gripping piece 15, the probe electrode and the jaw electrode do not short-circuit.

The transducer unit 8 has a transducer case 21 and ultrasonic transducer 22 provided in the transducer case 21. The ultrasonic transducer 22 extends from the inside of the transducer case 21 to the inside of the housing 5 and is proximally connected to the probe 13 in the housing 5. One end of the cable 4 is connected to the transducer case 21. The other end of the cable 4 is attachably and detachably connected to the control apparatus 3. Alternatively, the transducer case 21 is not provided, instead, the ultrasonic transducer 22 may be disposed in the housing 5. In this case, one end of the cable 4 is connected to the housing 5.

A rotatable knob 23 is attached to the housing 5. When the rotatable knob 23 is rotated, the sheath 6, the probe 13 including the first gripping piece 14, the second gripping piece 15, and the ultrasonic transducer 22 rotate together with the rotatable knob 23 around a central axis of the sheath 6 with respect to the housing 5. Accordingly, the angle of the end effector 7 around the central axis of the sheath 6 is adjusted. The rotatable knob 23 may not be provided.

The housing 5 is provided with an operation button 24. The operation button 24 is used to input an operation of supplying electric energy for generating ultrasonic vibration in the ultrasonic transducer 22 from the control apparatus 3 and input an operation of supplying electric energy for flowing a high frequency current in the end effector 7. Instead of the operation button 24 or in addition to the operation button 24, a foot switch (not illustrated) separately from the treatment apparatus 2 may be provided. Although only one operation button 24 is illustrated, a plurality of operation buttons 24 may be provided.

Figure 2:
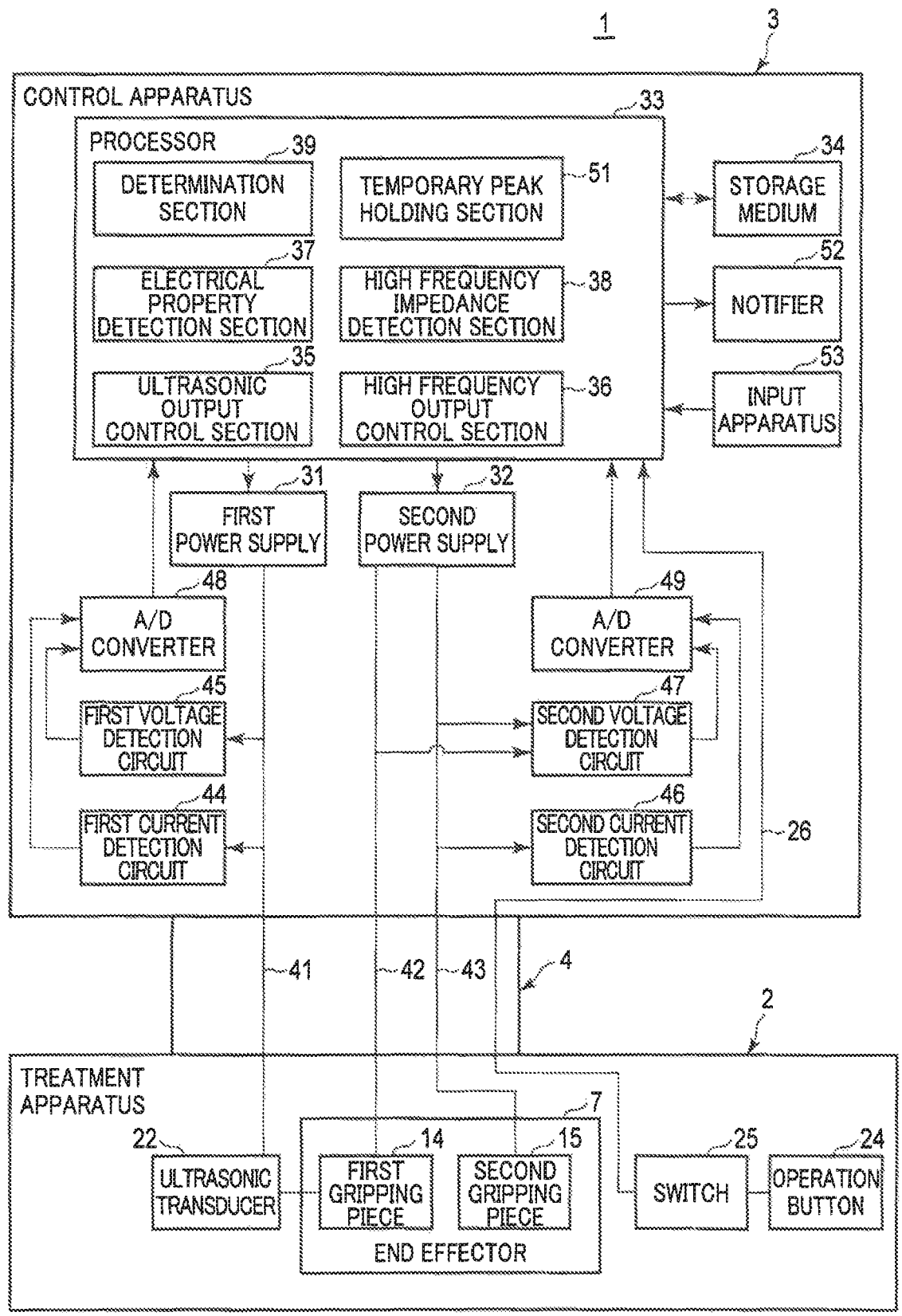
FIG. 2 is a schematic block diagram illustrating an example of the energy treatment system.

FIG. 2 is a schematic block diagram illustrating the treatment system 1. The control apparatus 3 has a first power supply 31 and a second power supply 32. The first power supply 31 is electrically connected to the ultrasonic transducer 22 via an electrical path 41 extending through the cable 4. The second power supply 32 is electrically connected to the first gripping piece 14 of the probe 13 via an electrical path 42 extending through the cable 4. The second power supply 32 is electrically connected to the second gripping piece 15 via an electrical path 43 extending through the cable 4, a conductive portion of the transducer case 21, and the sheath 6 (not illustrated in FIG. 2).

The first power supply 31 supplies electric energy for ultrasonically vibrating the ultrasonic transducer 22. The first power supply 31 has a conversion circuit or the like that converts electric power from a battery power supply or an electric outlet into electric energy to be supplied to the ultrasonic transducer 22. The second power supply 32 supplies electric energy for flowing a high frequency current to the end effector 7. The second power supply 32 also has a conversion circuit or the like that converts electric power from a battery power supply or an electric outlet into electric energy to be supplied to the end effector 7. The first power supply 31 and the second power supply 32 output the electric energy converted by the conversion circuits. The electric energy output from the first power supply 31 is supplied to the ultrasonic transducer 22 via the electrical path 41. The electric energy output from the second power supply 32 is supplied to the end effector 7 via the electrical paths 42 and 43. In this manner, the first power supply 31 is an ultrasonic power output unit that supplies vibration generation power to the ultrasonic transducer 22, and the second power supply 32 is a high frequency power output unit that supplies high frequency power to the first gripping piece 14 and the second gripping piece 15.

The control apparatus 3 has a processor (controller) 33 that controls the entire treatment system 1 and a storage medium 34. The processor 33 is formed from, for example, an integrated circuit including a central processing unit (CPU), an application specific integrated circuit (ASIC), or a field programmable gate array (FPGA). The processor 33 may be formed from one integrated circuit or a plurality of integrated circuits. The control apparatus 3 may be provided with one processor 33 or a plurality of separate processors 33. The processor 33 performs processing according to a program stored in the processor 33 or the storage medium 34. The storage medium 34 stores processing programs to be used by the processor 33 and parameters and tables to be used in operations by the processor 33.

The treatment apparatus 2 has a switch 25. The switch 25 operates in conjunction with an operation by the operation button 24 and is electrically connected to the processor 33 via an electrical path 26 extending through the cable 4. The switch 25 is provided in a detection circuit, for example, and is switched based on an input into the operation button 24. Specifically, the switch 25 is turned from OFF state to ON state by an operation input from the operation button 24. According to the turning of the switch 25 into the ON state, the processor 33 detects that an operation is input into the operation button 24.

The processor 33 has an ultrasonic output control section 35 and a high frequency output control section 36. The ultrasonic output control section 35 controls output of vibration generation power from the first power supply 31 based on an electrical signal transferred from the switch 25 by an input into the operation button 24, for example. The high frequency output control section 36 controls output of high frequency power from the second power supply 32 based on an electrical signal transferred from the switch 25 by an input into the operation button 24, for example.

When the electric energy is supplied from the first power supply 31 to the ultrasonic transducer 22 based on the control signal from the ultrasonic output control section 35, an alternating-current voltage applied from an electrode (not illustrated) in the ultrasonic transducer 22 to a piezoelectric element is converted into ultrasonic vibration, and thus ultrasonic vibration is generated in the ultrasonic transducer 22. The generated ultrasonic vibration is transferred in a direction from the proximal end to the distal end through the probe 13. Then, the probe 13, including the first gripping piece 14, generates ultrasonic vibration. The treatment apparatus 2 uses the ultrasonic vibration transferred to the first gripping piece 14 to perform treatment on the treatment target.

When electric energy is supplied from the second power supply 32 to the end effector 7, that is, the first gripping piece 14 functioning as the probe electrode and the second gripping piece 15 functioning as the jaw electrode, based on the control signal from the high frequency output control section 36, the high frequency voltage is applied between the first gripping piece 14 and the second gripping piece 15, and the high frequency current flows. The treatment apparatus 2 performs treatment on the treatment target by flowing the high frequency current between the first gripping piece 14 and the second gripping piece 15.

The control apparatus 3 has a first current detection circuit 44, a first voltage detection circuit 45, a second current detection circuit 46, a second voltage detection circuit 47, and analog/digital (A/D) converters 48 and 49. The first current detection circuit 44 detects output current from the first power supply 31 to the ultrasonic transducer 22. The first voltage detection circuit 45 detects output voltage from the first power supply 31 to the ultrasonic transducer 22. The second current detection circuit 46 detects output current from the second power supply 32 to the end effector 7. The second voltage detection circuit 47 detects output voltage from the second power supply 32 to the end effector 7. Transmitted to the A/D converters 48 and 49 are analog signals indicating the current values detected by the first current detection circuit 44 and the second current detection circuit 46 and analog signals indicating the voltage values detected by the first voltage detection circuit 45 and the second voltage detection circuit 47. The A/D converters 48 and 49 convert the received analog signals into digital signals and transmit the same to the processor 33.

The processor 33 has an electrical property detection section 37 and a high frequency impedance detection section 38. The electrical property detection section 37 (hereinafter, called property detection section 37) detects, temporally, an electrical property value of the ultrasonic transducer 22 based on signals of an output current and an output voltage received from the A/D converter 48. The electrical property value here refers to any of an electric impedance value of the ultrasonic transducer 22, a value of voltage applied to the ultrasonic transducer 22, a value of power supplied to the ultrasonic transducer 22, and others. The property detection section 37 detects (calculates) the electric impedance value, the voltage value, the power value, or the like of the ultrasonic transducer 22 as property value relating to the electric energy output from the first power supply 31 to the ultrasonic transducer 22. The following description is based on the assumption that the property detection section 37 detects the electric impedance value of the ultrasonic transducer 22 as electrical property value. However, the voltage value or the power value can also be used as electrical property value as described above. The electric impedance of the ultrasonic transducer 22 is herein called as "ultrasonic impedance". The high frequency impedance detection section 38 is a detection circuit, for example, that detects (calculates) the impedance value (high frequency impedance value) of the high frequency power between the first gripping piece 14 that is the probe electrode and the second gripping piece 15 that is the jaw electrode, based on the signals of the output current and the output voltage received from the A/D converter 49.

The processor 33 has a determination section 39. The determination section 39 is a determination circuit, for example, that makes a determination on output control based on the electrical property value detected by the property detection section 37, the high frequency impedance value detected by the high frequency impedance detection section 38, or the like. The ultrasonic output control section 35 and the high frequency output control section 36 control outputs of the first power supply 31 and the second power supply 32 based on the result of determination by the determination section 39.

The processor 33 also has a temporary peak holding section 51. The temporary peak holding section 51 holds the peak of the electrical property value, such as the maximum value (greatest value) of the ultrasonic impedance, determined by the determination section 39 based on the temporal change in the electrical property value detected by the property detection section 37.

In the present exemplary embodiment, while the electric energy is supplied from the first power supply 31 to the ultrasonic transducer 22, the ultrasonic output control section 35 controls output of the electric energy from the first power supply 31 by constant current control under which the output current is temporally kept constant. In this case, the output voltage from the first power supply 31 is adjusted in response to a change in the ultrasonic impedance value. Specifically, as the ultrasonic impedance increases, the output voltage is raised so that the output current is temporally kept constant. At this time, the output power also increases in response to the rise in the output voltage. In reverse, as the ultrasonic impedance decreases, the output voltage is lowered so that the output current is temporally kept constant. At this time, the output power also decreases in response to the reduction in the output voltage.

The control apparatus 3 has a notifier 52. The processor 33 includes a notification control section that controls the operation of the notifier 52 based on the result of determination by the determination section 39. The notifier 52 makes a notification to the user or the like by an acoustic notification such as a notification sound or the like from a beeper, a visual notification such as illumination or flickering of light or display of text or the like on a screen, or a combination of the foregoing notifications.

The ultrasonic output control section 35, the high frequency output control section 36, and the notification control section act as an output control section in the processor 33.

The control apparatus 3 has an input apparatus 53 that receives an instruction from an operator as a user. The input apparatus 53 is a touch panel, a keyboard, or the like. A user interface (not illustrated) sets various parameters stored in the storage medium 34 by an input operation from the input apparatus 53 or switches between ON and OFF states of various functions of the treatment apparatus 2, that is, switches between the kinds of operations or between the enabling and disabling of an operation.

Next, an operation for performing treatment on a treatment target by using the treatment system 1 will be described. First, the operator grips the fixed handle 11 and the movable handle 12 of the treatment apparatus 2. The operator then disposes the treatment target between the first gripping piece 14 and the second gripping piece 15 and closes the movable handle 12 to the fixed handle 11. Accordingly, the second gripping piece 15 is closed to the first gripping piece 14, and the treatment target is held between the first gripping piece 14 and the second gripping piece 15. The operator makes an operation input by the operation button 24. Accordingly, the switch 25 is turned to the ON state and the processor 33 detects the operation input from the operation button 24.

When the operation input from the operation button 24 is detected, the ultrasonic output control section 35 of the processor 33 causes the first power supply 31 to output electric energy to the ultrasonic transducer 22. Accordingly, the ultrasonic transducer 22 generates ultrasonic vibration that is transferred to the first gripping piece 14 through the probe 13. When the ultrasonic vibration is transferred to the first gripping piece 14 while the treatment target is gripped between the first gripping piece 14 and the second gripping piece 15, frictional heat is generated between the first gripping piece 14 and the treatment target. By this frictional heat, the treatment target is coagulated and incised at the same time.

When the operation input from the operation button 24 is detected, the high frequency output control section 36 of the processor 33 causes the second power supply 32 to output high frequency energy to the end effector 7. When the high frequency voltage is applied while the treatment target is gripped between the first gripping piece 14 and the second gripping piece 15, high frequency current flows to the treatment target. Then, Joule heat based on the resistance of the treatment target is generated, the treatment target is heated using the Joule heat, and incision is made during coagulation.

Figure 3:
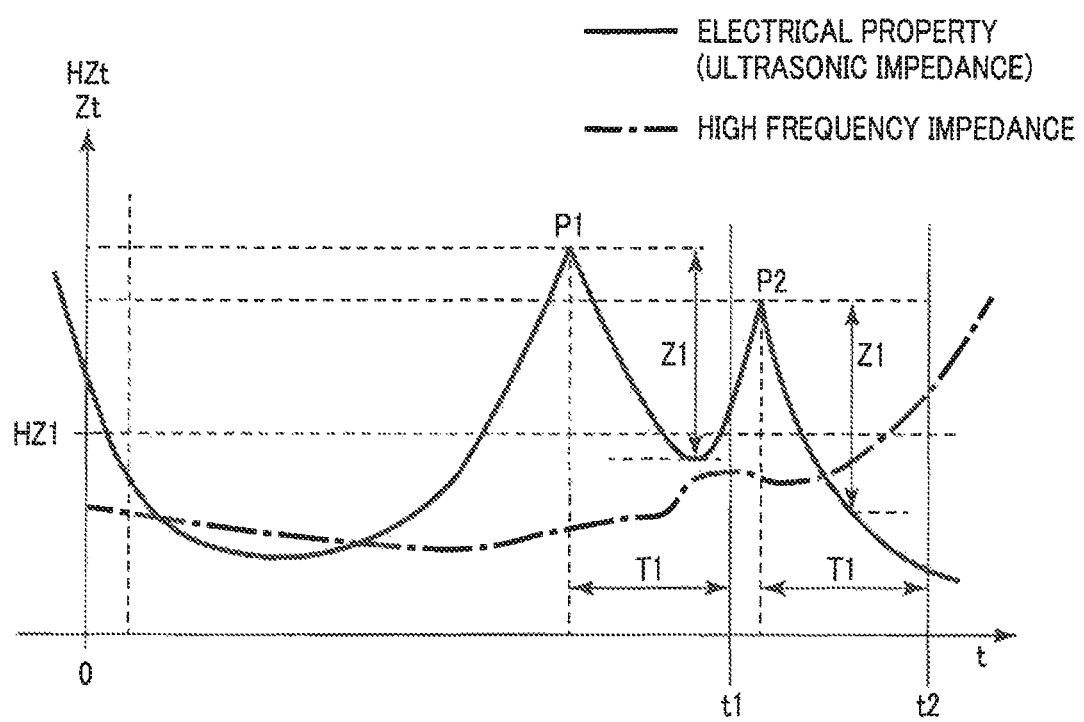
FIG. 3 is a diagram illustrating an example of temporal changes in electrical property and high frequency impedance of an ultrasonic transducer during treatment.

Next, the flow from the start of treatment to the end of treatment by the treatment system 1 will be described with reference to FIGS. 3 and 4. FIG. 3 is a diagram illustrating an example of temporal changes in ultrasonic impedance and high frequency impedance during treatment. FIG. 3 illustrates temporal changes in the ultrasonic impedance and the high frequency impedance when incising while coagulating a thick and hard body tissue with ultrasonic energy and high frequency energy using the treatment system 1. Here, it is determined that time is t, the ultrasonic impedance at the time t is $Zt=Z(t)$, and the high frequency impedance at the time t is $HZt=HZ(t)$.

At the treatment using the treatment system 1, as described above, the treatment target gripped between the gripping pieces 14 and 15 is incised while it is coagulated by the ultrasonic energy from the first gripping piece 14 and the high frequency energy from the first gripping piece 14 and the second gripping piece 15. The treatment target gripped between the gripping pieces 14 and 15 is divided in width directions of the end effector 7. The phenomenon that the treatment target is divided in the width directions of the end effector 7 is called herein "cut and division". When the treatment target gripped between the gripping pieces 14 and 15 is divided, the pad 17 of the second gripping piece 15 comes into contact with the first gripping piece 14.

During treatment, after the start of ultrasonic output, the ultrasonic impedance $Z(t)$ decreases once and then becomes stabled. The ultrasonic impedance $Z(t)$ decreases once because a moisture content of body tissue evaporates and protein denaturation starts in the body tissue, for example.

After that, when the treatment target is being incised while being coagulated by ultrasonic vibration, the ultrasonic impedance $Z(t)$ gradually increases until cut and division occurs in a part of the treatment target gripped between the gripping pieces 14 and 15. This is because, after protein denaturation in body tissue, the body tissue becomes coagulated and hardened to increase the frictional coefficient between the first gripping piece 14 and the body tissue increases, for example, and the first gripping piece 14 comes into contact with the pad 17 of the second gripping piece 15 to increase the frictional coefficient between the gripping pieces 14 and 15. The "gradual increase" here means that the ultrasonic impedance $Z(t)$ gradually increases with the progress of a time t, which includes the state that the ultrasonic impedance $Z(t)$ gradually increases with minute increases and decreases of several tens $\Omega$ or increases and decreases of more than $100\Omega$, for example.

After the gripped treatment target is cut and divided, ultrasonic impedance Z(t) gradually decreases. This is because, when the treatment target is cut and divided, the second gripping piece 15 is being closed to the first gripping piece 14 to decrease the amount of gripping force, for example, and the wear in the pad 17 of the second gripping piece 15 comes to a stabled state to decrease the frictional coefficient between the gripping pieces 14 and 15, for example. The "gradual decrease" here means that the ultrasonic impedance Z(t) gradually decreases with the progress of a time t, which includes the state that the ultrasonic impedance Z(t) gradually decreases with minute increases and decreases of several tens $\Omega$ or increases and decreases of more than 100$\Omega$, for example.

Therefore, it is possible to detect that the treatment target has been cut and divided, that is, the incision of the treatment target has completed, by detecting temporal changes in the ultrasonic impedance during treatment by the processor 33 of the control apparatus 3. For example, by detecting that the ultrasonic impedance has gradually decreased by a predetermined amount from the value (peak value, that maximum value) at the gradual transition from the gradual increase to the gradual decrease and that the predetermined time has elapsed since reaching the peak value. Although the behavior of the ultrasonic impedance is described here, it is possible to detect that the treatment target has been cut and divided in the same manner by using temporal changes in the electrical property value, such as the voltage applied from the first power supply 31 to the ultrasonic transducer 22 or the electric power supplied from the first power supply 31 to the ultrasonic transducer 22, instead of the ultrasonic impedance.

However, in the case of making an incision in thick or hard body tissue, such as cervix uteri, or making an incision in body tissue while slowly gripping the fixed handle 11 and the movable handle 12 of the treatment apparatus 2 by the operator, the body tissue gripped between the gripping pieces 14 and 15 is incised not at once but in a stepwise manner. Accordingly, in the foregoing cases, temporal changes in the electrical property value may become complicated, and a plurality of peaks (for example, a first peak P1 and a second peak P2 illustrated in FIG. 3) may be generated. For example, in FIG. 3, the electrical property value gradually increases from stabilization after output starting, and gradually decreases after reaching the first peak P1. At the time of the first peak P1 of the electrical property value, the body tissue as the treatment target is incised partially, but not completely cut and divided. The electrical property value gradually decreases after the first peak P1, then gradually increases again, and reaches the second peak P2. The body tissue is completely cut and divided at the time of the second peak P2.

Therefore, in the example illustrated in FIG. 3, the determination of incision completion by the processor 33 must be made at the time after the second peak P2. Otherwise, the body tissue gripped between the gripping pieces 14 and 15 is not cut and divided although the processor 33 determines that the incision is completed. In other words, for example, when the determination section 39 of the processor 33 makes a determination of incision completion based only on the first peak value of the electrical property value, there is a possibility that the determination section 39 determines that the incision has been completed although the incision has not yet been completed at the first peak P1. Specifically, at the time t1 illustrated in FIG. 3, when incision completion is made by detecting that the electrical property value has decreased from the peak value by a predetermined value and that a predetermined time has elapsed since the peak value was detected, there is actually a possibility that the treatment will be terminated even when the treatment target still remains.

FIG. 3 also illustrates an example of temporal changes in the ultrasonic impedance Z(t) and an example of temporal changes in the high frequency impedance HZ(t). It is known that the high frequency impedance HZ (t) is relatively low when the body tissue is not yet cut and divided, but rises as the incision progresses, and becomes relatively high when the body tissue is completely cut and divided. This is because, as the incision progresses, the properties and state of the body tissue between the gripping pieces 14 and 15 change, making it difficult for the high frequency current to flow therebetween.

In consideration of the above, in the present exemplary embodiment, the cut and division of the treatment target is determined based on the temporal change in the high frequency impedance and the electrical property value including the ultrasonic impedance, the voltage, and the electric power. Hereinafter, a flow of treatment by the treatment system 1 in the present exemplary embodiment, that is, processing performed by the processor 33 of the control apparatus 3 will be described.

Figure 4:
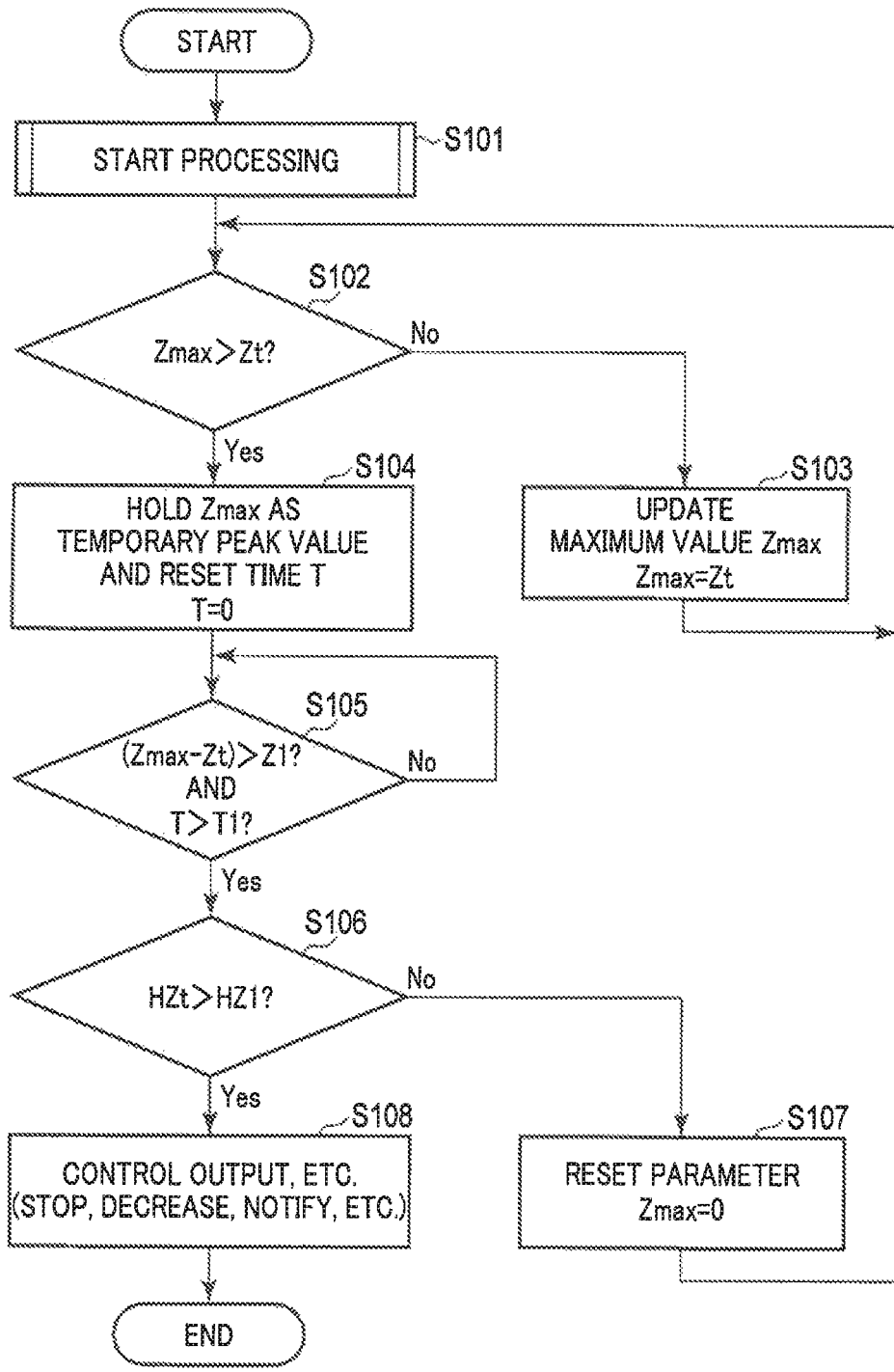
FIG. 4 is a diagram illustrating an example of a flow of treatment of the energy treatment system according to the first exemplary embodiment.

FIG. 4 is a flowchart illustrating an example of treatment by the treatment system 1 according to the first exemplary embodiment. The processor 33 first performs start processing (step S101). FIG. 5 is a flowchart illustrating start processing.

In the start processing, the processor 33 determines whether an operation input has been made from the operation button 24, that is, an operation input from the operation button 24 is ON or OFF based on whether the switch 25 is in the ON state (step S111). When no operation input has been made (No), the process returns to step S111. That is, the processor 33 waits until an operation input is made from the operation button 24. When an operation input has been made (Yes), the processor 33 resets parameters for determination such as a maximum value Zmax of the ultrasonic impedance Zt, a high frequency impedance HZt, and count time T (Zt=0, Zmax=0, HZt=0, T=0) (step S112).

After step S112, the ultrasonic output control section 35 causes the first power supply 31 to start output of electric energy to the ultrasonic transducer 22, and the high frequency output control section 36 causes the second power supply 32 to start output of electric energy to the end effector 7 (step S113). After the output is started, when a predetermined condition is satisfied, a phase locked loop (PLL) control is started. Under the PLL control, the frequency of the output of the electric energy from the first power supply 31 is adjusted such that a phase difference between the output current and the output voltage is less than a predetermined threshold. That is, the output frequency of the first power supply 31 is adjusted to match the resonant frequency of a vibration system. When the PLL control is started, the property detection section 37 starts detection of the ultrasonic impedance Zt as electrical property value with a lock-in (ultrasonic resonant frequency search completion) signal as a trigger, and also, the high frequency impedance detection section 38 starts detection of the high frequency impedance HZt (step S114). After step S114, the start processing is terminated, and the process moves to step S102.

After the start of the PLL control, the ultrasonic output control section 35 controls the output power from the first power supply 31 by the constant current control as described above under which the output current is temporally kept constant. When the output current is temporally kept constant, the amplitude and vibration speed of the ultrasonic wave generated in the ultrasonic transducer 22 also become temporally approximately constant, and the amplitude and vibration speed of the ultrasonic vibration in the first gripping piece 14 also become temporally approximately constant.

After the start of detection of the ultrasonic impedance Zt and the high frequency impedance HZt, the determination section 39 of the processor 33 determines whether the maximum value Zmax of the ultrasonic impedance is larger than the ultrasonic impedance Zt, that is, whether the ultrasonic impedance Zt starts to gradually decrease (step S102). When the maximum value Zmax is equal to or less than the ultrasonic impedance Zt (No), the processor 33 updates the maximum value Zmax of the ultrasonic impedance to the ultrasonic impedance Zt detected by the property detection section 37 (Zmax=Zt) (step S103). That is, the property detection section 37 monitors the temporal change in the ultrasonic impedance Zt, and the maximum value Zmax of the ultrasonic impedance from the start of ultrasonic output by the electric energy from the first power supply 31 is updated. The processor 33 repeats steps S102 and S103 until the ultrasonic impedance Zt gradually decreases.

In step S102, when it is determined that the maximum value Zmax is larger than the ultrasonic impedance Zt (Yes), the temporary peak holding section 51 of the processor 33 holds the maximum value Zmax as the temporary peak value of the ultrasonic impedance, and the processor 33 resets the count time T (T=0) (step S104).

After step S104, the determination section 39 determines whether a gradually decreasing value Zmax−Zt of the ultrasonic impedance Zt from the maximum value Zmax of the ultrasonic impedance is larger than a gradual decrease definite threshold Z1 (for example, illustrated in FIG. 3) (first condition), and determines whether the count time T since the maximum value Zmax starts to be held is large than a temporal threshold T1 (for example, illustrated in FIG. 3) (second condition) (step S105).

The threshold Z1 and the time T1 may be prescribed values stored in advance in the Storage medium 34. These prescribed values can be, for example, lookup tables (LUT) showing a relationship between the threshold Z1 and the time T1 set to each model of the treatment apparatus 2. For example, the treatment apparatus 2 has a storage medium (not illustrated) in which identification information of the treatment apparatus 2 is stored. The identification information refers to information for identifying the model (model number) of the treatment apparatus 2, for example, and may be the serial number of the treatment apparatus 2. When the treatment apparatus 2 is connected to the control apparatus 3 via the cable 4, the processor 33 reads the identification information from the storage medium in the treatment apparatus 2. The processor 33 specifies the model of the treatment apparatus 2 based on the read identification information, and reads the values of the threshold Z1 and the time T1 corresponding thereto from the LUT and sets the same. Alternatively, the treatment apparatus 2 may, have a storage medium (not illustrated) in which the threshold Z1 and the time T1 corresponding to the model of the treatment apparatus 2 is stored. In this case, when the treatment apparatus 2 is connected to the control apparatus 3 via the cable 4, the processor 33 reads the threshold Z1 and the time T1 from the storage medium in the treatment apparatus 2 and sets the same. Alternatively, the threshold Z1 and the time T1 may be set by an operator making an input from the input apparatus 53 based on a temporal change in the ultrasonic impedance Zt.

In step S105, when the first condition and the second condition are satisfied (Yes), the process moves to next step S106. When not satisfied (No), the process returns to step S105 again. That is, the processor 33 repeatedly performs step S105 until it is determined that the determination section 39 satisfies the first condition and the second condition. The first condition and the second condition do not need to be simultaneously satisfied at a certain time t. For example, as illustrated in FIG. 3, the determination section 39 can determine that the two conditions are satisfied when the gradually decreasing value Zmax−Zt from the maximum value Zmax of the ultrasonic impedance at the time t before the time t1 is larger than the set threshold Z1 and when the count time T at the time t1 is equal to the set time T1, and the process may move to step S106. That is, at the time t1, the process moves to step S106.

After the process moves to Yes in step S105, the determination section 39 determines whether the high frequency impedance HZt is larger than the threshold HZ1 (for example, illustrated in FIG. 3) (step S106). As described above, in the present exemplary embodiment, the determination section 39 performs incision completion determination using the temporal change in the high frequency impedance HZt in step S106 in addition to the incision completion determination using the temporal change in the ultrasonic impedance Zt in step S105. The threshold HZ1 may be a prescribed value stored in advance in the storage medium 34, or may be a value set by an input by the operator from the input apparatus 53 based on the temporal change in the high frequency impedance HZt. As described above with respect to the threshold Z1 and the time T1, it may be a value set to each model.

In step S106, when it is determined that the high frequency impedance HZt is equal to or less than the threshold HZ1 (No), the incision has not yet been completed, that is, the treatment target is not completely cut and divided according to the incision completion determination based on the temporal change in the high frequency impedance HZt by the determination section 39. That is, although incision completion is determined based on the incision completion determination based on the temporal change in the ultrasonic impedance Zt, incision completion determination based on the temporal change in the high frequency impedance HZt is not determined as incision completion. That is, since the treatment target is not yet cut and divided, and thereafter, the treatment target is completely cut and divided, it is considered that the ultrasonic impedance Zt turns from gradual increase to gradual decrease and the peak of the ultrasonic impedance Zt appears. When it is determined in step S106 that the high frequency impedance HZt is equal to or less than the threshold HZ1 (No), the processor 33 resets the maximum value Zmax of the ultrasonic impedance (Zmax=0) (step S107), and the process returns to step S102. That is, since the incision of the treatment target has not yet been completed, the processor 33 clears the maximum value Zmax of the ultrasonic impedance, which is an internal variable used for control, and starts monitoring the temporal change in the ultrasonic impedance Zt again by the property detection section 37.

For example, at the time t1 illustrated in FIG. 3, in the incision completion determination based on the ultrasonic impedance Zt in step S105, the determination section 39 determines that the incision of the treatment target has been completed. However, in next step S105, since the high frequency impedance HZt at the time t1 is equal to or less than the threshold HZ1, the determination section 39 determines that the incision of the treatment target has not yet been completed (step S106-No). Therefore, in step S107, the processor 33 resets the maximum value Zmax of the ultrasonic impedance, and the process returns to step S102. That is, the processor 33 starts monitoring again the temporal change in the ultrasonic impedance Zt. After the peak P2 of the ultrasonic impedance Zt appears, the determination section 39 determines whether the gradually decreasing value Zmax−Zt of the ultrasonic impedance from the new maximum value Zmax which is the peak value thereof is larger than the threshold Z1, and determines whether the count time T from the start of holding the new maximum value Zmax is longer than the time T1.

On the other hand, when the determination section 39 determines in step S106 that the high frequency impedance HZt is larger than the threshold HZ1 (Yes), it is determined that the treatment object has been cut and divided from not only the temporal change in the ultrasonic impedance but also the temporal change in the high frequency impedance. Therefore, the ultrasonic output control section 35 and the high frequency output control section 36 of the processor 33 control outputs of the first power supply 31 and the second power supply 32 (step S108). After step S108, the flow of treatment is terminated.

For example, in step S108, the ultrasonic output control section 35 automatically stops the output of the electric energy from the first power supply 31, and the high frequency output control section 36 automatically stops the output of the electric energy from the second power supply 32. Alternatively, in step S108, the ultrasonic output control section 35 decreases the output of the electric energy from the first power supply 31. Accordingly, the amplitude of the ultrasonic vibration of the first gripping piece 14 in the probe 13 is decreased. Alternatively, in step S108, the processor 33 transmits, to the notifier 52, a control signal for operating the notifier 52. Accordingly, the notifier 52 makes a notification (an acoustic notification, a visual notification, or a combination of the foregoing notifications as described above). The notification may be singly made or may be made in combination with the automatic output stop or output decrease. When the notification is to be singly made, the operator cancels the operation input from the operation button 24 based on this so that the switch 25 turns from the ON state to the OFF state. According to the turning of the switch 25 to the OFF state, the ultrasonic output control section 35 of the processor 33 causes the first power supply 31 to stop the output of the electric energy to the ultrasonic transducer 22.

In the foregoing description, in a case where the treatment target is incised by using the coagulation incision action by ultrasonic vibration in the treatment system 1, the peak of the electrical property value that is the ultrasonic impedance appears when the treatment target is cut and divided, for example. In the present exemplary embodiment, in response to the conventional algorithm for detecting the peak, various parameters for incision completion detection are optimized by using feedback based on the temporal change in the high frequency impedance. That is, in the present exemplary embodiment, the treatment system 1 optimizes cut and division detection based on a feedback value due to the temporal change in the high frequency impedance, in addition to detection of the cut and division based on peak detection of electrical property values including ultrasonic impedance, voltage, and electric power.

Accordingly, for example, at the time t1 illustrated in FIG. 3, it is determined that the incision has been completed in the conventional technique in which incision completion determination is made based on only the temporal change in the electrical property value. However, according to the present exemplary embodiment, the determination section 39 of the processor 33 detects that the high frequency impedance is lower than the threshold even if it is determined that the incision is completed as a result of the incision completion determination based on the temporal change in the electrical property value, and it can be determined that incision has not yet been completed at the time t1. That is, according to the present exemplary embodiment, the processor 33 can avoid erroneous detection of the incision completion when a plurality of peaks appear in the temporal change in the electrical property value, for example, when a thick and hard body tissue is incised.

Further, for example, at the time t2 illustrated in FIG. 3, the processor 33 can detect that the incision is completed based on the monitoring of the temporal change in the high frequency impedance by the high frequency impedance detection section 38. Therefore, according to the present exemplary embodiment, it is possible to reliably determine that the treatment target is completely cut and divided.

In addition, according to the present exemplary embodiment, the ultrasonic output control section 35 and the high frequency output control section 36 of the processor 33 stop the outputs of the first power supply 31 and the second power supply 32 after the complete cut and division of the treatment target to prevent the treatment target from being left cut and divided.

According to the present exemplary embodiment, after the treatment target is completely cut and divided, the ultrasonic output control section 35 stops or decreases the output of the electric energy from the first power supply 31. This effectively prevents the pad 17 of the second gripping piece 15 from coming into contact with the first gripping piece 14 while the first gripping piece 14 ultrasonically vibrates with a large amplitude and vibration speed. Therefore, the wearing down and deformation of the pad 17 of the second gripping piece 15 are effectively prevented.

As described above, in the present exemplary embodiment, the processor 33 appropriately detects the timing at which the treatment target is cut and divided. Based on the detected appropriate timing, the output of the electric energy from the first power supply 31 is stopped or decreased, or a notification is made to notify that it should be stopped or decreased.

In the present exemplary embodiment, in the incision completion determination based on the temporal change in the high frequency impedance (step S106), the determination section 39 compares an absolute value of the high frequency impedance with a predetermined threshold. However, for example, the determination section 39 may determine that the treatment target has been cut and divided by comparing a difference of the high frequency impedance value from the high frequency impedance value at a certain time t with a predetermined threshold.

In the present exemplary embodiment, in the treatment system 1 capable of outputting ultrasonic vibration energy and high frequency energy in combination, the impedance of the high frequency energy output from the treatment apparatus 2 that coagulates incision of the treatment target is used for incision completion determination. However, the impedance of the high frequency energy used for determining the incision completion is not limited to that output for coagulation incision of the treatment target. For example, even in the treatment system 1 including the ultrasonic treatment apparatus performing the coagulation incision only by the ultrasonic vibration, the incision completion determination as in the treatment system 1 as described above can be made by specially flowing the high frequency current and monitoring the high frequency impedance for incision completion determination. In this case, the current flowed for the incision completion determination is not necessarily the high frequency current, and the processor 33 may have an impedance detection section instead of the high frequency impedance detection section.

In the foregoing description, when it is determined that the incision has not been completed in the incision completion determination based on the temporal change in the high frequency impedance, the processor 33 resets the maximum value Zmax of the electrical property value and starts monitoring the temporal change in the electrical property value again by the property detection section 37. However, when it is determined that the incision has not been completed in the incision completion determination based on the temporal change in the high frequency impedance, the processing performed by the processor 33 is not limited thereto. Hereinafter, another processing performed when it is determined that the incision has not been completed in the incision completion determination based on the temporal change in the high frequency impedance will be described as modifications.

First Exemplary Embodiment: First Modification

Figure 6:
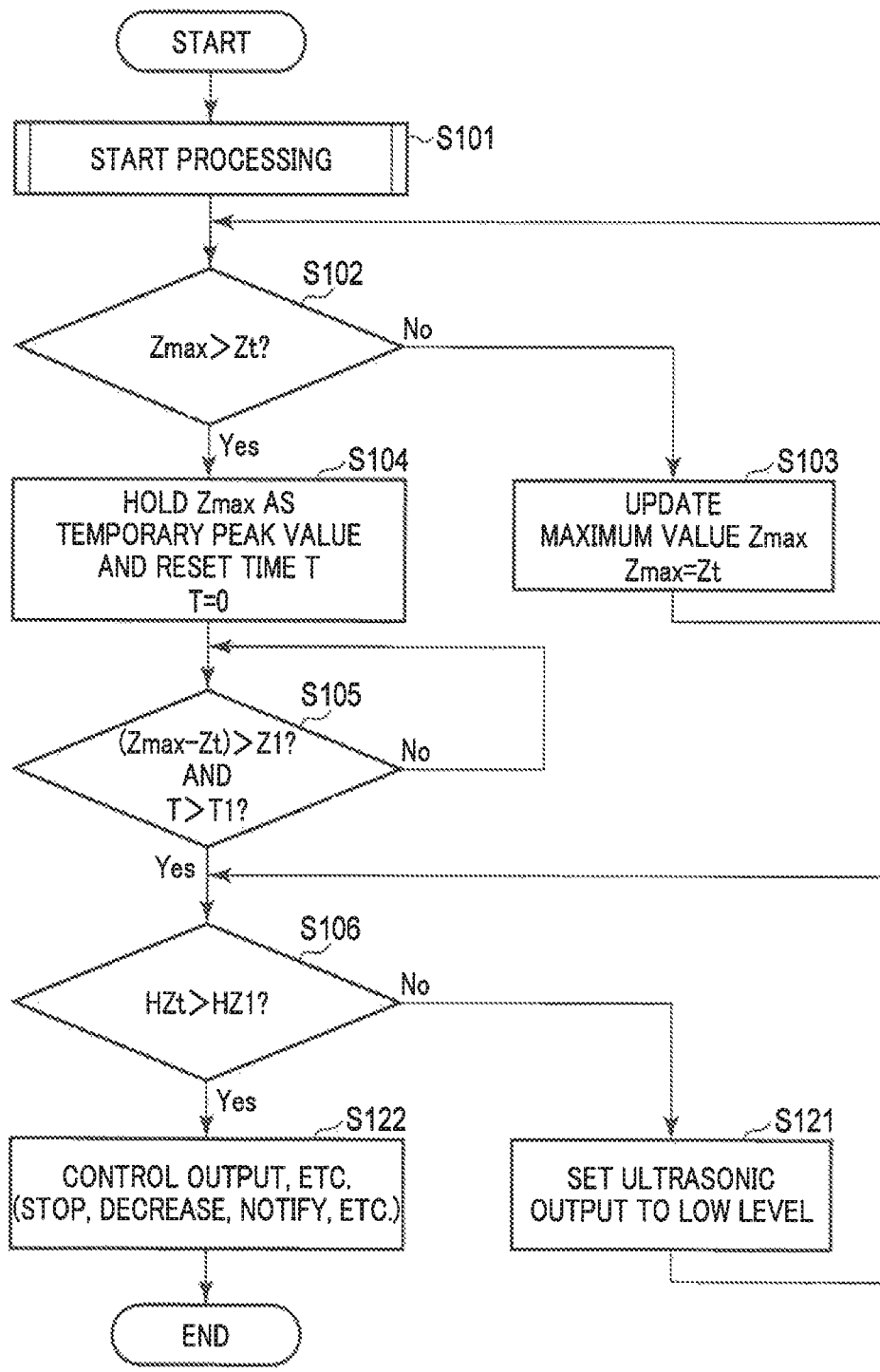
FIG. 6 is a diagram illustrating an example of a flow of treatment of an energy treatment system according to a first modification of the first exemplary embodiment.

FIG. 6 is a flowchart illustrating an example of treatment by a treatment system 1 according to a first modification of the first exemplary embodiment. Steps S101 to S106 are the same as the flow illustrated in FIG. 4.

In step S106, when the determination section 39 determines that the high frequency impedance HZt is equal to or less than the threshold HZ1 (No), the ultrasonic output control section 35 sets the electric energy output from the first power supply 31 to the ultrasonic transducer 22 to a low level (step S121). That is, the ultrasonic output control section 35 weakens the amplitude of the ultrasonic vibration of the first gripping piece 14. After step S121, the process returns to step S106, and again, the determination section 39 determines whether the high frequency impedance HZt is larger than the threshold HZ1. That is, the output of the ultrasonic wave is maintained at a low level until the high frequency impedance HZt is larger than the threshold HZ1.

On the other hand, in step S106, when the determination section 39 determines that the high frequency impedance HZt is larger than the threshold HZ1 (Yes), the ultrasonic output control section 35 and the high frequency output control section 36 control the outputs or the like of the first power supply 31 and the second power supply 32 (step S122). For example, in step S122, the ultrasonic output control section 35 automatically stops the output of the electric energy from the first power supply 31, and the high frequency output control section 36 automatically stops the output of the electric energy from the second power supply 32. Alternatively, in step S122, the ultrasonic output control section 35 decreases the output of electric energy from the first power supply 31. Alternatively, in step S122, the processor 33 activates the notifier 52 to make a notification. After step S122, the flow of treatment is terminated.

As described above, when it is determined that the high frequency impedance HZt is equal to or less than the threshold HZ1, the ultrasonic output control section 35 decreases the electric energy output from the first power supply 31 to the ultrasonic transducer 22, and it is effectively prevented that the first gripping piece 14 vibrating due to the ultrasonic vibration continues contacting the pad 17 of the second gripping piece 15 with a large amplitude and vibration speed while a part of the treatment target gripped between the gripping pieces 14 and 15 is cut and divided. Accordingly, the wearing down and deformation of the pad 17 of the second gripping piece 15 are effectively prevented.

In step S121, the ultrasonic output control section 35 may decrease the electric energy output from the first power supply 31 to the ultrasonic transducer 22, and the high frequency output control section 36 may increase the electric energy output from the second power supply 32 to the end effector 7. This also makes it possible to compensate for the decrease in the output of the ultrasonic vibration energy with the output of the high frequency energy to reliably incise the treatment target while preventing the wearing down and deformation of the pad 17 of the second gripping piece 15.

First Exemplary Embodiment: Second Modification

FIG. 7 is a flowchart illustrating an example of treatment by a treatment system 1 according to a second modification of the first exemplary embodiment. Steps S101 to S106 and S108 are the same as the flow illustrated in FIG. 4. In step S106, when the determination section 39 determines that the high frequency impedance HZt is equal to or less than the threshold HZ1 (No), the processor 33 changes the threshold Z1 of the ultrasonic impedance to Z2 to set the same as a new threshold Z1 and changes the set time T1 to T2 to set the same as a new set time T1 (step S123). That is, the processor 33 changes the gradual decrease definite threshold Z1 and the temporal threshold T1, which are parameters for detecting incision completion. Like the threshold Z1 and the time T1, the threshold Z2 and the time T2 may be prescribed values stored in advance in the storage medium 34, may be a value read from the storage medium 34 corresponding to the model of the treatment apparatus 2, and may be a value read from the storage medium of the treatment apparatus 2.

After step S123, the process returns to step S105, and again, the determination section 39 determines that the gradually decreasing value Zmax−Zt of the ultrasonic impedance Zt from the maximum value Zmax of the ultrasonic impedance (the value of the ultrasonic impedance Zt at the peak P1) is larger than the new threshold Z1 (that is, the threshold Z2), and determines whether the count time T from the start of holding the maximum value Zmax (from the peak P1) is larger than the new time T1 (that is, the time T2) (step S105). That is, after the processor 33 changes the threshold Z1 and the set time T1, the determination section 39 determines the cut and division again based on the temporal change in the ultrasonic impedance.

As described above, when it is determined that the high frequency impedance HZt is equal to or less than the threshold HZ1, the processor 33 may change the threshold Z1 and the time T1 that are determination parameters, may monitor the temporal change in the electrical property value again to make an incision completion determination, and may reliably determine that the treatment target has been completely cut and divided.

As described above, in the present exemplary embodiment, when the determination section 39 determines in step S106 that the high frequency impedance HZt is equal to or less than the threshold HZ1 (No), the processor 33 clears the internal variables of electrical property (for example, ultrasonic impedance, voltage, power) control as appropriate to monitor the tissue incision state again (FIG. 4: first exemplary embodiment), decreases the ultrasonic output (FIG. 6: first modification), and changes the parameter of the incision completion detection (FIG. 7: second modification). Accordingly, it is possible to provide the energy treatment system capable of appropriately detecting that the incision of the treatment target has been completed due to the cut and division, and preventing the incision from remaining.

In the foregoing description, the processor 33 calculates the maximum value Zmax as the peak of the electrical property value and determines the completion of incision by using the elapsed time from the peak or the gradually decreasing value, but the determination of the completion of incision using the temporal change in the electrical property value can also be made by using the time change rate or the integrated value of the electrical property value. Hereinafter, the cut and division determination using the time change rate and the cut and division determination using the integrated value will be respectively described.

First Exemplary Embodiment: Third Modification

Figure 8:
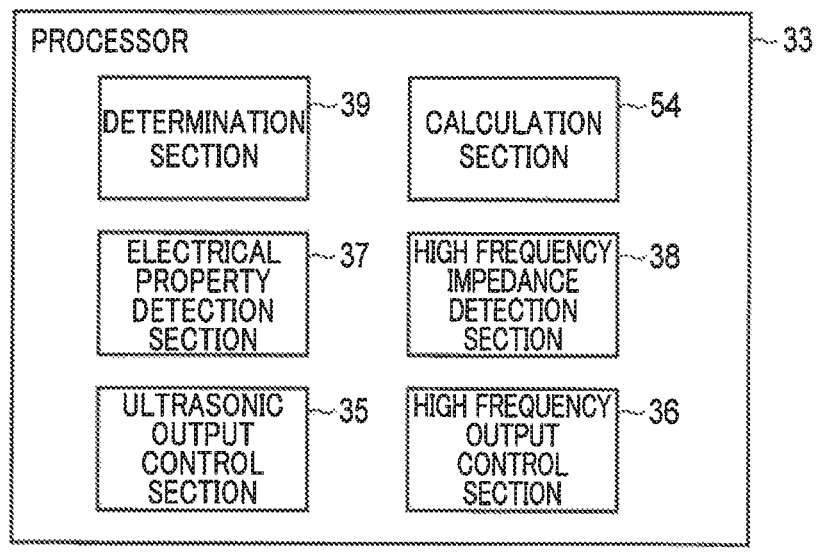
FIG. 8 is a block diagram illustrating an example of a processor.

FIG. 8 is a block diagram illustrating an example of the processor 33. The processor 33 has an ultrasonic output control section 35, a high frequency output control section 36, an electrical property detection section 37, a high frequency impedance detection section 38, a determination section 39, and a calculation section 55.

Figure 9:
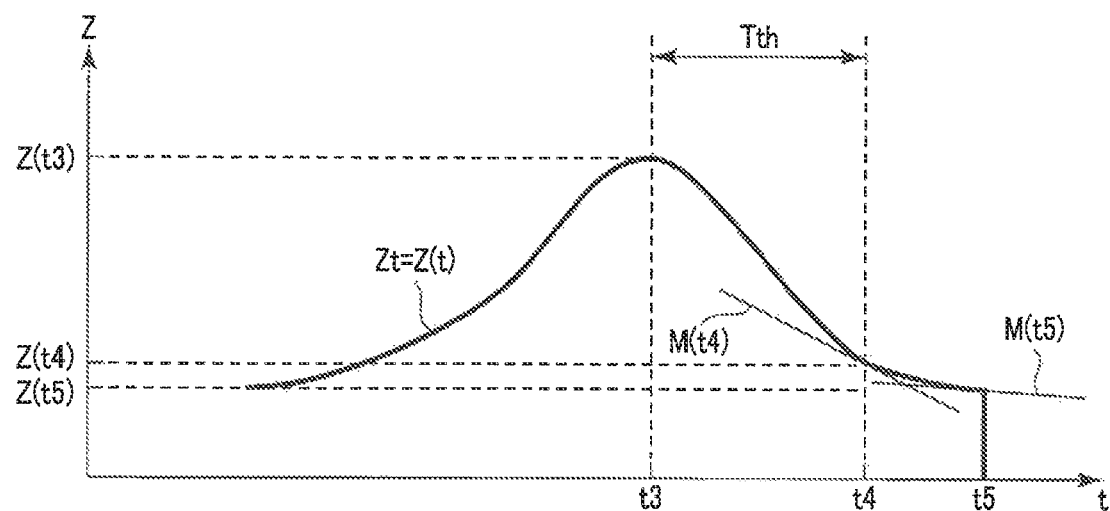
FIG. 9 is a diagram illustrating an example of temporal changes in electrical property of an ultrasonic transducer so as to show the concept of incision completion determination by using a temporal change rate.

FIG. 9 is a diagram illustrating an example of temporal changes in the ultrasonic impedance Zt during treatment. The ultrasonic impedance Zt=Z (t) gradually increases until time t3 and gradually decreases after time t3. The time t3 is a gradual decrease start time at which the gradual decrease starts after the ultrasonic impedance Zt gradually increases. At the time t3 or immediately therearound, the cut and division occurs in the treatment target gripped between the first gripping piece 14 and the second gripping piece 15.

A time when a predetermined time Tth has elapsed from the time t3 that is the gradual decrease start time is set to t4. At time t5 after the time t4, a time change rate $\Delta Z(t5)$ of an ultrasonic impedance $Z(t5)$ is larger than a predetermined threshold $\Delta Zth$. That is, at the time t5, the time change rate $\Delta z(t)$ is switched from a state equal to or less than the predetermined threshold $\Delta Zth$ to a state larger than the time change rate $\Delta Z(t)$. At the time t5 or immediately therearound, the treatment target gripped between the first gripping piece 14 and the second gripping piece 15 is completely cut and divided. The time change rate $\Delta Z(t4)$ at the time t4 is equal to or less than the predetermined threshold $\Delta Zth$. FIG. 4 illustrates a tangential line M(t4) of the ultrasonic impedance Z(t4) at the time t4 and a tangential line M(t5) of the ultrasonic impedance M(t5) at the time t5. A slope of the tangential line M(t4) is the time change rate $\Delta Z(t4)$ at the time t4, and a slope of the tangential line M(t5) is the time change rate $\Delta Z(t5)$ at the time t5.

Figure 10:
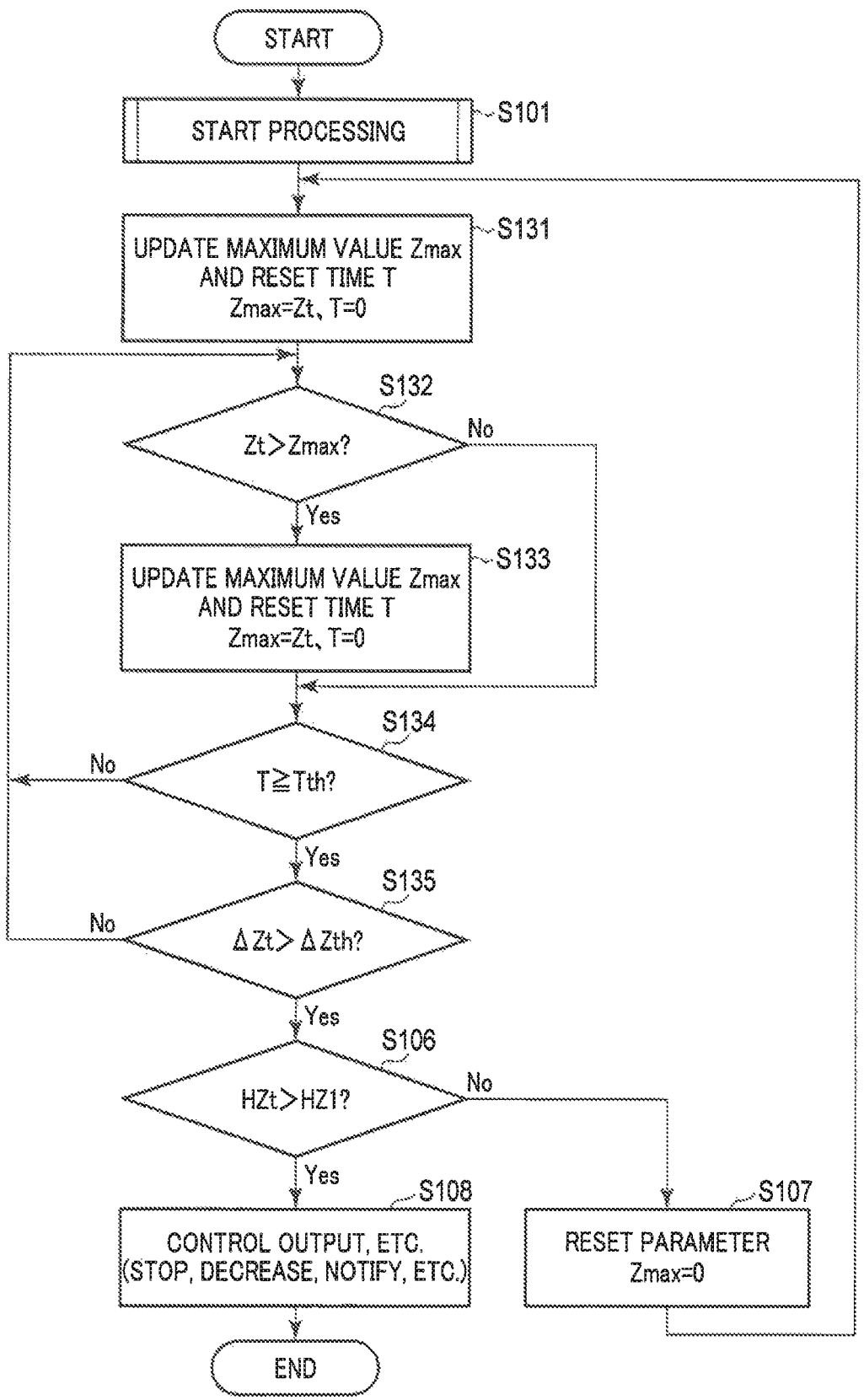
FIG. 10 is a diagram illustrating an example of a flow of treatment of an energy treatment system according to a third modification of the first exemplary embodiment.

FIG. 10 is a flowchart illustrating an example of treatment by a treatment system 1 according to a third modification of the first exemplary embodiment. Steps S101 and S106 to S108 are the same as the flow illustrated in FIG. 4.

After the start processing, the processor 33 updates the maximum value Zmax of the ultrasonic impedance to the ultrasonic impedance Zt detected by the property detection section 37, and resets the time T (Zt=Zmax, T=0) (step S131). After step S131, the determination section 39 of the processor 33 determines whether the ultrasonic impedance is larger than the maximum value Zmax of the ultrasonic impedance updated in step S131, that is, whether the ultrasonic impedance Zt starts to gradually decrease (step S132).

When the ultrasonic impedance Zt is larger than the maximum value Zmax (Yes), the processor 33 updates the maximum value Zmax and resets the count time T (T=0) (step S133). Then, the process moves to step S134. When the ultrasonic impedance Zt is less than the maximum value Zmax (No), the process moves to step S134. That is, when the ultrasonic impedance Zt is less than the maximum value Zmax, the processor 33 holds the maximum value Zmax without updating and does not reset the count time T.

Then, the determination section 39 determines whether the count time T is equal to or longer than a predetermined time Tth (step S135). The predetermined time Tth is also a prescribed value or the like stored in advance in the storage medium 34. When the count time T is shorter than the predetermined time Tth (No), the process returns to step S132. On the other hand, when the count time T is equal to or longer than the predetermined time Tth (Yes), the calculation section 55 calculates the time change rate $\Delta Z(t)$ of the ultrasonic impedance Z(t). Then, the determination section 39 determines whether the calculated time change rate $\Delta Z(t)$ is larger than the threshold $\Delta Zth$ (step S135). Here, the threshold $\Delta Zth$ is a negative value and is set to a value close to zero (for example, −1). The threshold $\Delta Zth$ is also a prescribed value or the like stored in advance in the storage medium 34.

In step S134, when it is determined that the time change rate $\Delta Z(t)$ is not larger than the threshold $\Delta Zth$ (No), the process returns to step S132. On the other hand, when it s determined that the time change rate $\Delta Z(t)$ is larger than the threshold $\Delta Zth$ (Yes), the process moves to step S106. Then, the determination section 39 determines whether the high frequency impedance HZt is larger than a preset threshold HZ1 (step S106). Since the subsequent processing (steps S106 to S108) is the same as the flow illustrated in FIG. 4, the description thereof will be omitted.

First Exemplary Embodiment: Fourth Modification

Figure 11:
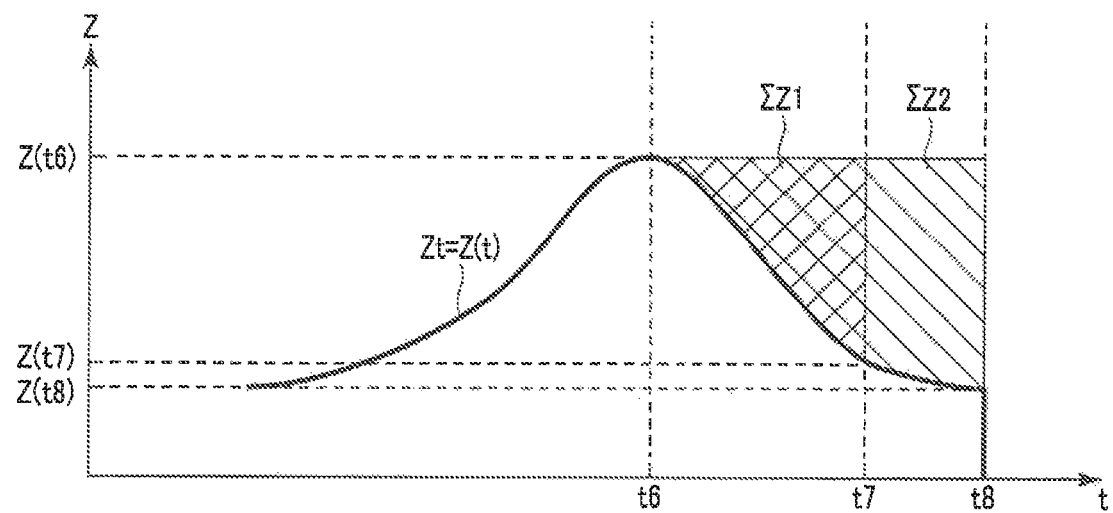
FIG. 11 is a diagram illustrating an example of temporal changes in electrical property of an ultrasonic transducer so as to show the concept of incision completion determination by using an integrated value.

FIG. 11 is a diagram illustrating an example of temporal changes in the ultrasonic impedance Zt during treatment. The ultrasonic impedance Zt=Z (t) gradually increases until time t6 and gradually decreases after time t6. The time t6 is a gradual decrease start time at which the gradual decrease starts after the ultrasonic impedance Zt gradually increases. At the time t6 or immediately therearound, the cut and division occurs in the treatment target gripped between the first gripping piece 14 and the second gripping piece 15.

A time t7 after the time t6 and a time t8 after the time t7 are defined. The integrated value $\Sigma(Zmax-Z(t))$ of the amount of change in the ultrasonic impedance from the time t6 to the time t7 is the integrated value $\Delta Z1$, and the integrated value $\Sigma(Zmax-Z(t))$ of the amount of change in the ultrasonic impedance from the time t6 to the time t8 is the integrated value $\Sigma Z2$. The integrated value $\Sigma Z1$ is equal to or less than the threshold. $\Sigma Zth$, and the integrated value $\Sigma Z2$ is larger than the threshold $\Sigma Zth$. The integrated value $\Sigma(Zmax-Z(t))$ from the time t6 that is the gradual decrease start time of the difference value $Zmax-Z(t)$ is switched from the state equal to or lower than the threshold $\Sigma Zth$ to the state larger than the threshold $\Sigma Zth$ at the time t8. Then, at the time t8 or immediately therearound, the treatment target gripped between the first gripping piece 14 and the second gripping piece 15 is completely cut and divided. In FIG. 11, the area of the portion enclosed by the straight line t=t7, the straight line $Z=Z(t6)$, and the curve $Z=Z(t)$ is the integrated value $\Sigma Z1$ of the difference value $(Zmax-Z(t))$ from the time t6 to the time t7. The area of the portion enclosed by the straight line t=t8, the straight line Z=z(t6), and the curve Z=Z(t) is the integrated value ΣZ2 of the difference value (Zmax−Z(t)) from the time t6 to the time t8.

Figure 12:
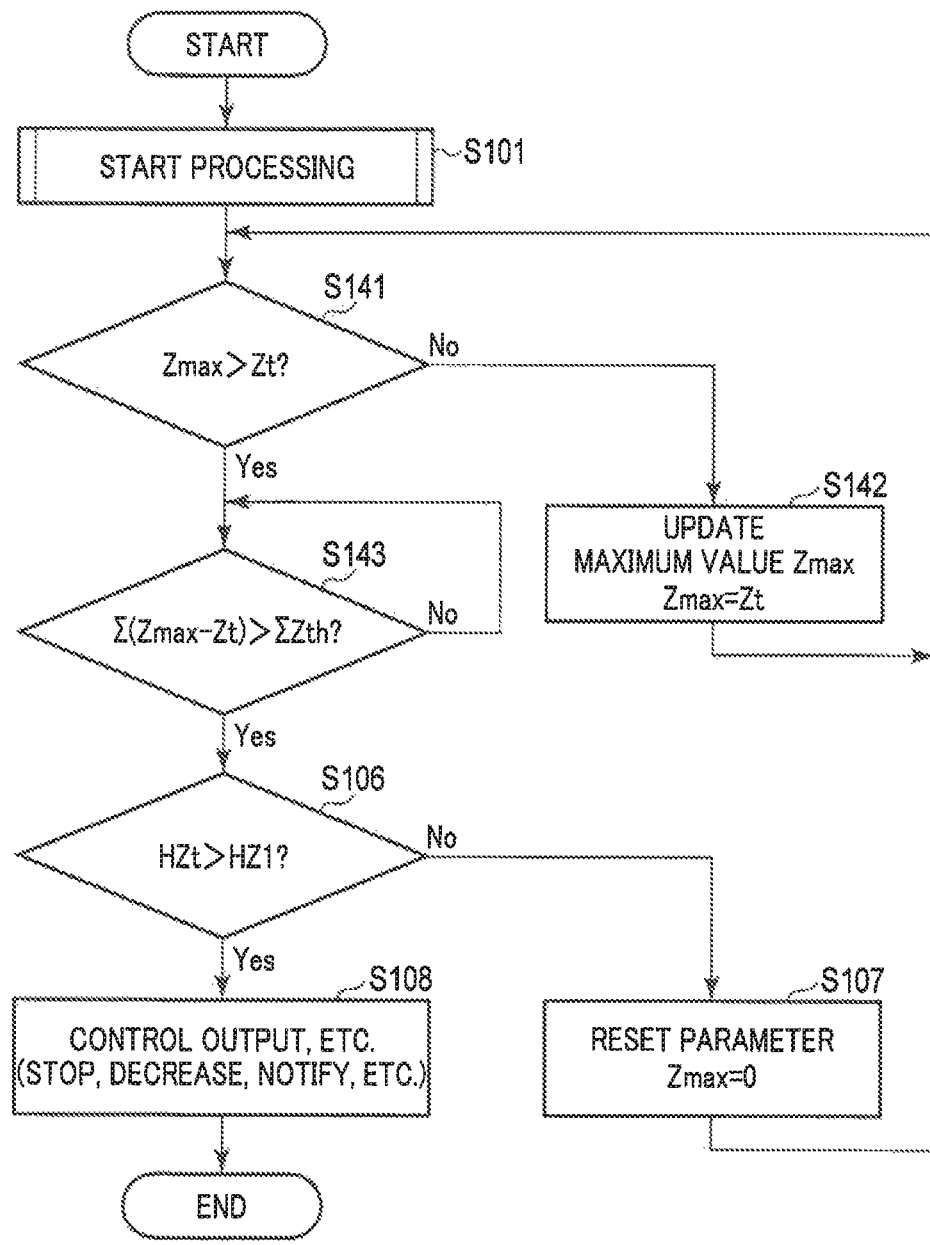
FIG. 12 is a diagram illustrating an example of a flow of treatment of an energy treatment system according to a fourth modification of the first exemplary embodiment.

FIG. 12 is a flowchart illustrating an example of treatment by a treatment system 1 according to a fourth modification of the first exemplary embodiment. In steps S101 and S106 to S108, although similar to the flow illustrated in FIG. 4, the control parameters to be reset in step S112 are three parameters of the ultrasonic impedance Zt, the maximum value Zmax, and the high frequency impedance HZt, and the count time T is unnecessary.

After the start processing, the determination section 39 of the processor 33 determines whether the maximum value Zmax of the ultrasonic impedance is larger than the ultrasonic impedance Zt, that is, whether the ultrasonic impedance Zt starts to gradually decrease (step S141). When the maximum value Zmax is equal to or less than the ultrasonic impedance Zt (No), the processor 33 updates the maximum value Zmax of the ultrasonic impedance to the ultrasonic impedance Zt detected by the property detection section 37 (Zmax=Zt) (step S142). That is, the property detection section 37 monitors the temporal change in the ultrasonic impedance Zt, and the maximum value Zmax of the ultrasonic impedance from the start of ultrasonic output by the electric energy from the first power supply 31 is updated. The processor 33 repeats steps S141 and S142 until the ultrasonic impedance Zt gradually decreases.

In step S141, when it is determined that the maximum value Zmax is larger than the ultrasonic impedance Zt (Yes), the process moves to step S143. That is, when the ultrasonic impedance Zt is less than the maximum value Zmax, the processor 33 holds the maximum value Zmax without updating.

The processor 33 detects the time point when the ultrasonic impedance Zt is switched from the state equal to or larger than the maximum value Zmax to the state less than the maximum value Zmax as the gradual decrease start time at which the gradual decrease starts after the ultrasonic impedance Z gradually increases. The calculation section 55 of the processor 33 calculates the difference value Zmax−Z(t) obtained by subtracting the ultrasonic impedance Z(t) from the peak value of the ultrasonic impedance Z(t) at the gradual decrease start time that is the maximum value Zmax, and calculates the integrated value Σ(Zmax−Z(t)) from the gradual decrease start time of the difference value Zmax−Z(t). Then, the determination section 39 determines whether the integrated value Σ(Zmax−Z(t)) calculated from the gradual decrease start time to the time t is larger than the threshold ΣZth (step S143). Here, the threshold ΣZth is a positive value. The threshold ΣZth is also a predetermined value or the like stored in advance in the storage medium 34.

When it is determined in step S143 that the integrated value Σ(Zmax−Z(t)) is not larger than the threshold ΣZth (No), the process returns to step S143. On the other hand, when it is determined that the integrated value Σ(Zmax−Z(t)) is larger than the threshold ΣZth (Yes), the process moves to step S106. Then, the determination section 39 determines whether the high frequency impedance HZt is larger than a preset threshold HZ1 (step S106). Since the subsequent processing (steps S106 to S108) is the same as the flow illustrated in FIG. 4, the description thereof will be omitted.

As described above, the incision completion determination using the temporal change in the electrical property of the ultrasonic transducer is not limited to the detection of the maximum value of the electrical property value, and may be made by calculating the time change rate in the electrical property value (third modification) or the integrated value of the electrical property value (fourth modification). Accordingly, the third modification and the fourth modification can also obtain the same effects as those described above with respect to the present exemplary embodiment.

Second Exemplary Embodiment

Figure 14:
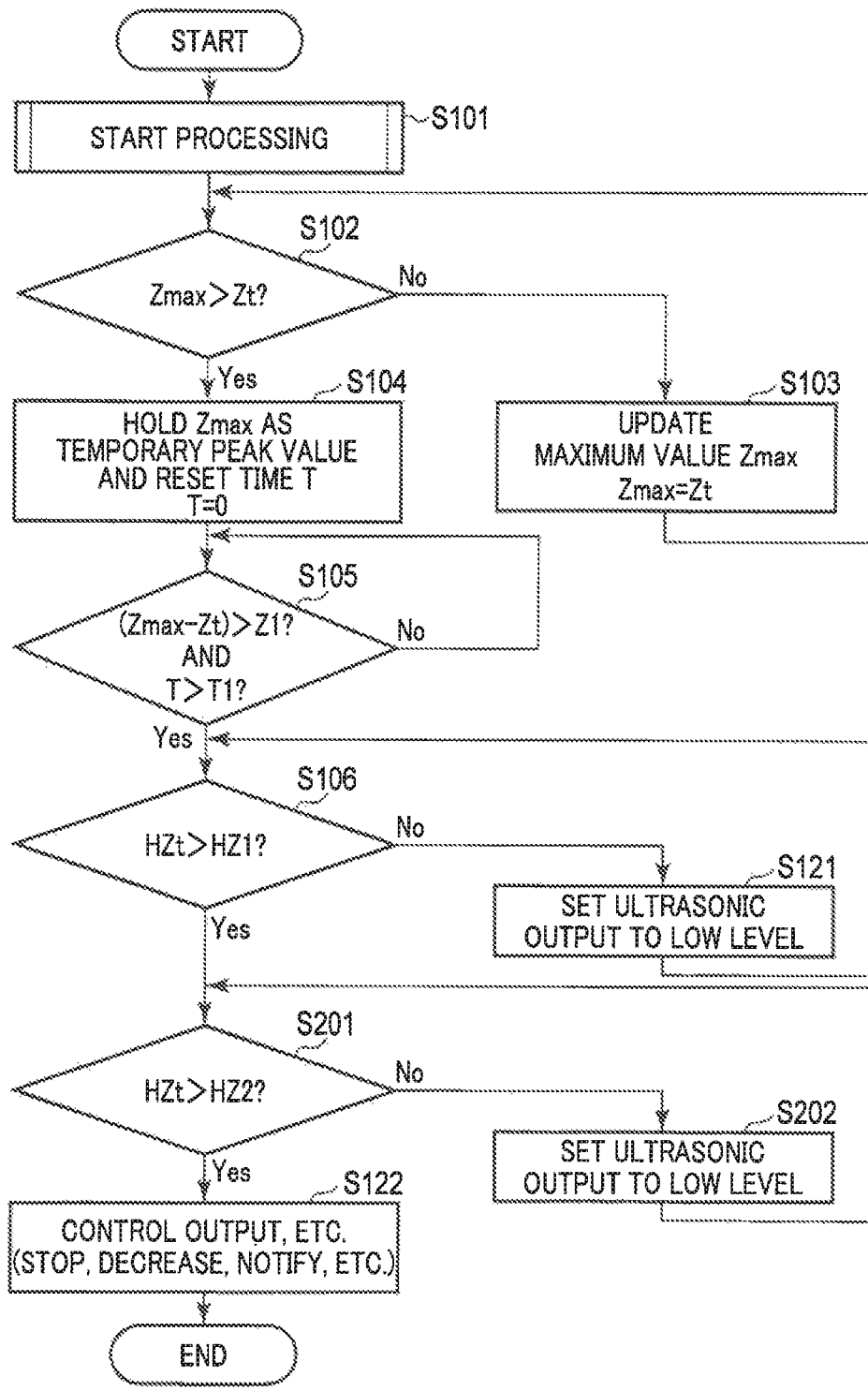
FIG. 14 is a diagram illustrating an example of a flow of treatment of an energy treatment system according to a second exemplary embodiment.

A second exemplary embodiment will be described with reference to FIGS. 13 to 15. Hereinafter, the same configuration and operation as in the first exemplary embodiment will not be described, and differences from the first exemplary embodiment will be described.

FIG. 13 is a diagram illustrating temporal changes in ultrasonic impedance and high frequency impedance during treatment by a treatment system 1. FIG. 14 is a flowchart illustrating an example of treatment by the treatment system 1 according to the second exemplary embodiment. In the present exemplary embodiment, steps S101 to S106 and S121 are the same as in the first exemplary embodiment. In the present exemplary embodiment, a plurality of thresholds of the high frequency impedance are set, and incision completion determination based on the temporal change in the high frequency impedance is performed a plurality of number of times.

After the process moves to Yes in step S105, a determination section 39 determines whether the high frequency impedance HZt is larger than a first threshold HZ1 (for example, illustrated in FIG. 13) (step S106). When it is determined that the high frequency impedance HZt is equal to or less than the first threshold HZ1 (No), an ultrasonic output control section 35 sets the electric energy output from a first power supply 31 to an ultrasonic transducer 22 to a low level (step S121). That is, the ultrasonic output control section 35 weakens the amplitude of the ultrasonic vibration of a first gripping piece 14. For example, the ultrasonic output control section 25 decreases the electric energy output from the first power supply 31 by 10% (for example, 90%) from the initial value or the immediately previous value. After step S121, the process returns to step S106, and again, the determination section 39 determines whether the high frequency impedance HZt is larger than the first threshold HZ1. On the other hand, when the determination section 39 determines that the high frequency impedance HZt is larger than the first threshold HZ1 (Yes in step S106), the process moves to step S201.

Then, the determination section 39 determines whether the high frequency impedance HZt is larger than a second threshold HZ2 (for example, illustrated in FIG. 13) (step S201). Here, the second threshold is larger than the first threshold (HZ1<HZ2). When it is determined that the high frequency impedance HZt is equal to or less than the second threshold HZ2 (No), the ultrasonic output control section 35 sets the electric energy output from the first power supply 31 to the ultrasonic transducer 22 to a lower level (step S202). That is, the ultrasonic output control section 35 further weakens the amplitude of the ultrasonic vibration of the first gripping piece 14. For example, the ultrasonic output control section 35 decreases the electric energy output from the first power supply 31 by 20% (for example, 80%) from the initial value or the immediately previous value. After step S202, the process returns to step S201, and again, the determination section 39 determines whether the high frequency impedance HZt is larger than the second threshold HZ2.

On the other hand, when it is determined in step S201 that the high frequency impedance HZt is larger than the second threshold HZ2 (Yes), the process moves to step S122. Then, the ultrasonic output control section 35 and a high frequency output control section 36 control output and the like (step S122). After step S122, the flow of treatment is terminated.

As described above, in the second exemplary embodiment, the plurality of thresholds of the high frequency impedance, for example, two thresholds HZ1 and HZ2 of the high frequency impedance are set, the incision completion detection is performed based on the gradual decrease amount from the peak of the electrical property value and the count time, and then, the incision completion detection is performed based on the plurality of thresholds of the high frequency impedance. According to the present exemplary embodiment, it is possible to provide the energy treatment system that reduces undesirable effects such as damage to the treatment target or the pad of the second gripping piece, while reliably incising the treatment target, by providing the plurality of thresholds of the high frequency impedance and performing stepwise control of the output of ultrasonic waves.

Second Exemplary Embodiment: Modification

Figure 15:
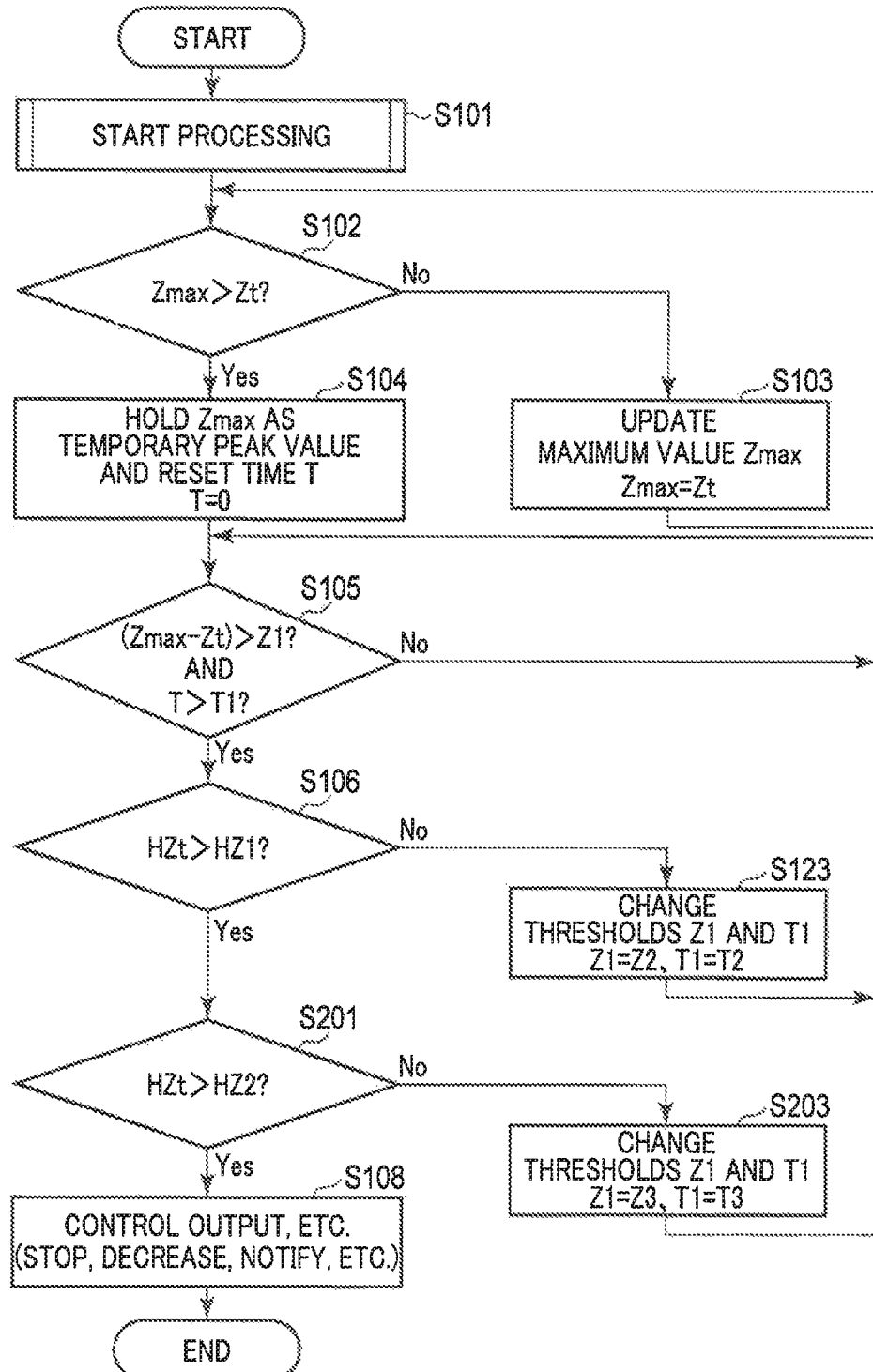
FIG. 15 is a diagram illustrating an example of a flow of treatment of an energy treatment system according to a modification of the second exemplary embodiment.

FIG. 15 is a flowchart illustrating an example of treatment by a treatment system 1 according to a modification of the second exemplary embodiment. In the present exemplary embodiment, steps S101 to S106 and S123 are the same as in the second modification of the first exemplary embodiment.

After the process moves to Yes in step S105, the determination section 39 determines whether the high frequency impedance HZt is larger than a first threshold HZ1 (for example, illustrated in FIG. 13) (step S106). When it is determined that the high frequency impedance HZt is equal to or less than the first threshold HZ1 (No), the processor 33 changes the first threshold Z1 of the ultrasonic impedance to Z2 to set the same as a new threshold Z1 and changes the set time T1 to T2 to set the same as a new set time T1 (step S123). That is, the processor 33 changes the gradual decrease definite threshold Z1 and the temporal threshold T1, which are parameters for detecting incision completion.

After step S123, the process returns to step S105, and again, the determination section 39 determines whether the gradually decreasing value Zmax−Zt of the ultrasonic impedance Zt from the maximum value Zmax of the ultrasonic impedance is larger than the threshold Z1 (for example, illustrated in FIG. 13) (first condition), and determines whether the count time T from the start of holding the maximum value Zmax is larger than the time T1 (for example, illustrated in FIG. 13) (second condition) (step S105). That is, after the processor 33 changes the threshold Z1 and the set time T1, the determination section 39 determines the cut and division again based on the temporal change in the ultrasonic impedance. On the other hand, when it is determined in step S106 that the high frequency impedance HZt is larger than the first threshold HZ1 (No), the process moves to step S201.

Then, the determination section 39 determines whether the high frequency impedance HZt is larger than a second threshold HZ2 (for example, illustrated in FIG. 13) (step S201). When it is determined that the high frequency impedance HZt is equal to or less than the second threshold HZ2 (No), the processor 33 changes the threshold Z1 of the ultrasonic impedance to Z3 to set the same as a new threshold Z1 and changes the set time T1 to T3 to set the same as a new set time T1 (step S203). That is, the processor 33 changes the gradual decrease definite threshold Z1 and the temporal threshold T1, which are parameters for detecting incision completion.

After step S203, the process returns to step S105, and again, the determination section 39 determines whether the gradually decreasing value Zmax−Zt of the ultrasonic impedance Zt from the maximum value Zmax of the ultrasonic impedance is larger than the threshold Z1 (for example, illustrated in FIG. 13) (first condition), and determines whether the count time T from the start of holding the maximum value Zmax is larger than the time T1 (for example, illustrated in FIG. 13) (second condition) (step S105). That is, after the processor 33 changes the threshold Z1 and the set time T1, the determination section 39 determines the cut and division again based on the change in the ultrasonic impedance.

On the other hand, when it is determined in step S201 that the high frequency impedance HZt is larger than the second threshold HZ2 (No), the process moves to step S108. Then, the ultrasonic output control section 35 and the high frequency output control section 36 control output and the like (step S108). After step S108, the flow of treatment is terminated.

In the present modification, the same effect as described in the second exemplary embodiment can be obtained. In the example illustrated in FIG. 14, the ultrasonic output control section 35 decreases the ultrasonic output in steps S121 and S202, and in the example illustrated in FIG. 15, the processor 33 changes the thresholds Z1 and T1 in steps S123 and S203, but these can be combined. Specifically, for example, the ultrasonic output control section 35 may set the ultrasonic output to the low level after the cut and division determination relating to the first threshold HZ1 of the high frequency impedance, and the processor 33 may change the thresholds Z1 and T1 after the cut and division determination relating to the second threshold HZ2 of the high frequency impedance.

Third Exemplary Embodiment

A third exemplary embodiment will be described with reference to FIGS. 16 and 17. Hereinafter, the same configuration and operation as in the first exemplary embodiment will not be described, and differences from the first exemplary embodiment will be described. In the present exemplary embodiment, the processor 33 constantly monitors the temporal change in the high frequency impedance regardless of the temporal change in the ultrasonic impedance, and appropriately adjusts the ultrasonic output based on this change.

In the first exemplary embodiment and the second exemplary embodiment, a determination section 39 of a processor 33 determines that the treatment target has been cut and divided by the incision completion determination based on the temporal change in the electrical property value, and then makes the incision completion determination based on the temporal change in the high frequency impedance value. The incision completion determination using the temporal change in the high frequency impedance value is not limited to those supplementary or complementary to the incision completion determination using the temporal change in the electrical property value. In the present exemplary embodiment, the determination section 39 of the processor 33 makes the incision completion determination that is a combination of the cut and division determination using the temporal change in the electrical property value and the cut and division determination based on the temporal change in the high frequency impedance value. In the third exemplary embodiment, as an example of the incision completion determination made by combining these two determinations, the processor 33 constantly monitors the temporal change in the high frequency impedance value and makes the incision completion determination based on the temporal change in the electrical property value.

Figure 16:
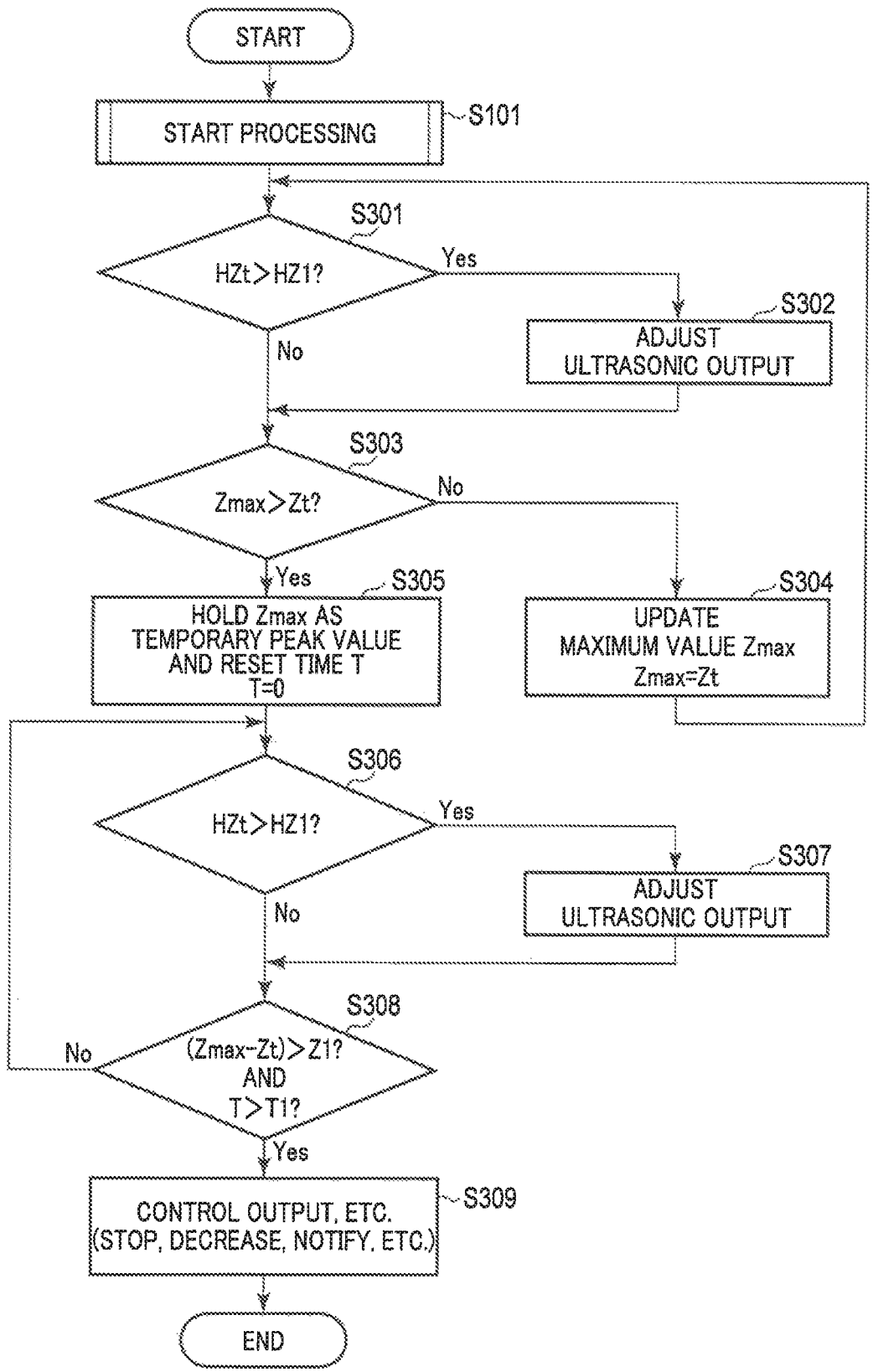
FIG. 16 is a diagram illustrating an example of a flow of treatment of an energy treatment system according to a third exemplary embodiment.
Figure 17:
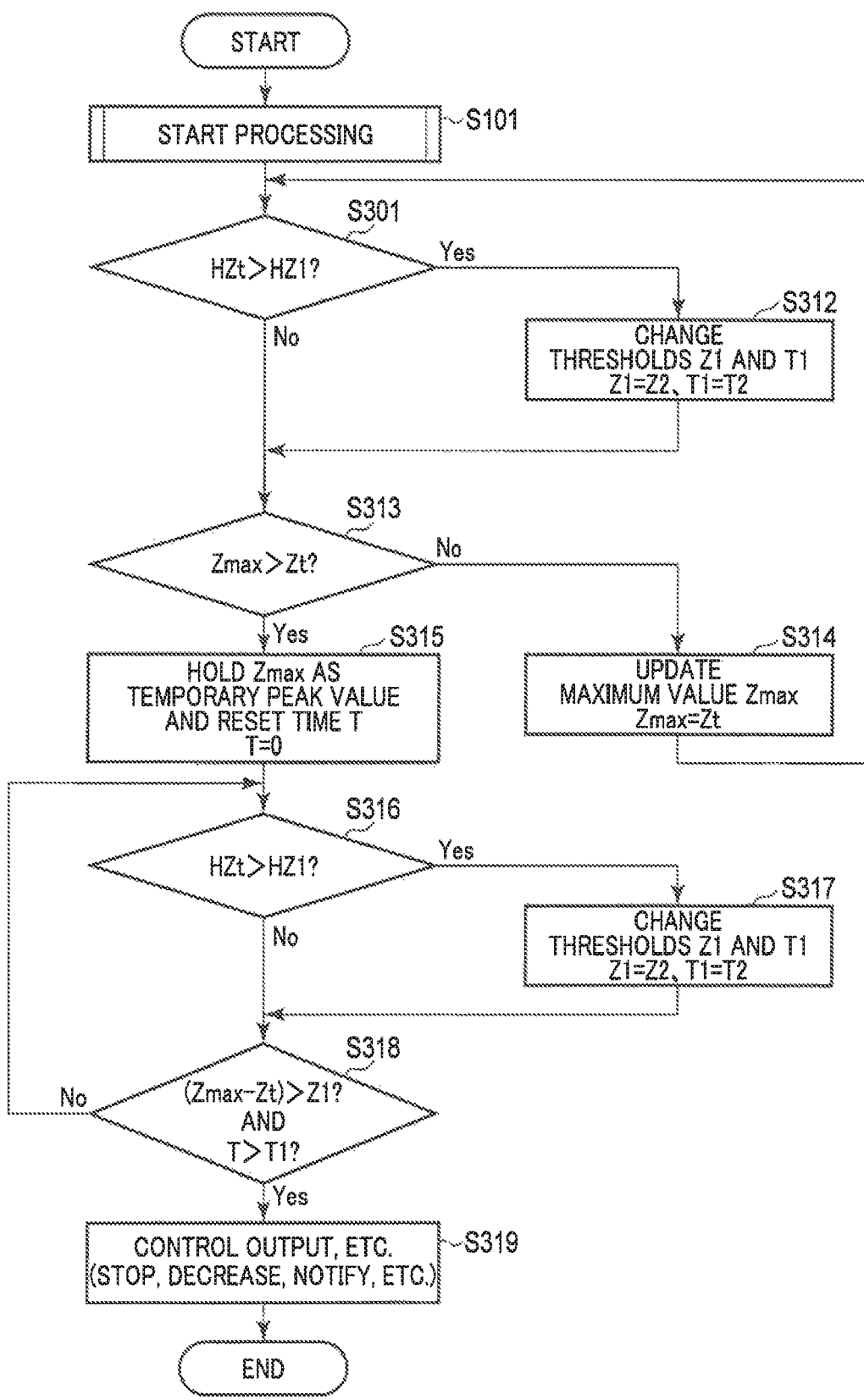
FIG. 17 is a diagram illustrating an example of a flow of treatment of an energy treatment system according to a modification of the third exemplary embodiment.

FIG. 16 is a flowchart illustrating an example of treatment by the treatment system 1 according to the third exemplary embodiment. First, the processor 33 performs the same start processing as in the first exemplary embodiment and the second exemplary embodiment (step S101).

After step S101, the determination section 39 of the processor 33 determines whether the high frequency impedance HZt is larger than the threshold HZ1 (step S301). In the present exemplary embodiment, the determination section 39 monitors whether the high frequency impedance value detected by the high frequency impedance detection section 38 is larger than the threshold HZ1 always, that is, even before the cut and division determination using the electrical property value is made.

When it is determined in step S301 that the high frequency impedance HZt is equal to or less than the threshold HZ1 (No), the process moves to step S303. On the other hand, when it is determined that the high frequency impedance HZt is larger than the threshold HZ1 (Yes), the process moves to step S302. Then, the ultrasonic output control section 35 adjusts the electric energy output from the first power supply 31 to the ultrasonic transducer 22 (step S302). In the present exemplary embodiment, even before it is determined that the incision has been completed in the incision completion detection using the ultrasonic impedance value, the determination section 39 adjusts the ultrasonic output to, for example, a low level based on the temporal change in the high frequency impedance value. Therefore, the ultrasonic output control section 35 weakens the amplitude of the ultrasonic vibration of the first gripping piece 14. Then, the process moves to step S303.

In step S303, the determination section 39 determines whether the maximum value Zmax of the ultrasonic impedance is larger than the ultrasonic impedance Zt, that is, whether the ultrasonic impedance Zt starts to gradually decrease. When the maximum value Zmax is equal to or less than the ultrasonic impedance Zt (No), the processor 33 updates the maximum value Zmax of the ultrasonic impedance to the ultrasonic impedance Zt detected by the property detection section 37 (Zmax=Zt) (step S304). Then, the process returns to step S301. That is, the processor 33 repeatedly performs steps S301 to S304 until the determination section 39 determines that the ultrasonic impedance Zt is less than the threshold Zmax. On the other hand, when it is determined that the maximum value Zmax is larger than the ultrasonic impedance Zt (Yes), the process moves to step S305. Then, the temporary peak holding section 51 of the processor 33 holds the maximum value Zmax as the temporary peak value of the ultrasonic impedance, and the processor 33 resets the count time T (T=0) (step S305).

After step S305, the determination section 39 of the processor 33 determines whether the high frequency impedance HZt is larger than the threshold HZ1 (step S306). When it is determined that the high frequency impedance HZt is equal to or less than the threshold HZ1 (No), the process moves to step S308. On the other hand, when it is determined that the high frequency impedance HZt is larger than the threshold HZ1 (Yes), the process moves to step S307. Then, the ultrasonic output control section 35 adjusts the electric energy output from the first power supply 31 to the ultrasonic transducer 22 (step S307). As described above, even before it is determined that the incision has been completed in the incision completion detection using the ultrasonic impedance value, the determination section 39 adjusts the ultrasonic output to, for example, a low level based on the temporal change in the high frequency impedance value. Therefore, the ultrasonic output control section 35 weakens the amplitude of the ultrasonic vibration of the first gripping piece 14. Then, the process moves to step S308.

In step S308, the determination section 39 determines whether the gradually decreasing value Zmax−Zt of the ultrasonic impedance Zt from the maximum value Zmax of the ultrasonic impedance is larger than the threshold Z1 (first condition), and determines whether the count time T from the start of holding the maximum value Zmax is larger than the time T1 (second condition). When it is determined that the first condition and the second condition are not satisfied (No), the process returns to step S306. That is, the processor 33 repeatedly performs steps S306 to S308 until the determination section 39 determines that the first condition and the second condition are satisfied.

On the other hand, when it is determined in step S308 that the first condition and the second condition are satisfied (Yes), the process moves to step S309. Then, the ultrasonic output control section 35 and the high frequency output control section 36 control output and the like (step S309). After step S309, the flow of treatment is terminated.

As described above, in the third exemplary embodiment, the temporal change in the high frequency impedance is constantly monitored, and the ultrasonic output control section 35 appropriately adjusts the electric energy output from the first power supply 31 to the ultrasonic transducer 22 based on the monitored temporal change in the high frequency impedance. Accordingly, while the treatment is progressed, it is effectively prevented that the first gripping piece 14 vibrating due to the ultrasonic vibration continues contacting the pad 17 of the second gripping piece 15 with a large amplitude and vibration speed. Accordingly, the wearing down and deformation of the pad 17 of the second gripping piece 15 are effectively prevented.

In the third exemplary embodiment, as in the first exemplary embodiment and the second exemplary embodiment, the incision completion determination is made by combining the determination using the temporal change in the electrical property value and the determination using the temporal change in the high frequency impedance, and it is possible to appropriately detect that the treatment target has been cut and divided and to prevent the cut remainder from being left Third Exemplary Embodiment: Modification FIG. 17 is a flowchart illustrating an example of treatment by a treatment system 1 according to a modification of the third exemplary embodiment. First, the processor 33 performs the same start processing as in the first exemplary embodiment and the second exemplary embodiment (step S101).

After step S101, the determination section 39 of the processor 33 determines whether the high frequency impedance HZt is larger than the threshold HZ1 (step S301). In the present modification, the determination section 39 monitors whether the high frequency impedance value detected by the high frequency impedance detection section 38 is larger than the threshold HZ1 always, that is, even before the cut and division determination using the electrical property value is made.

When it is determined in step S301 that the high frequency impedance HZt is equal to or less than the threshold HZ1 (No), the process moves to step S313. On the other hand, when it is determined that the high frequency impedance HZt is larger than the threshold HZ1 (Yes), the process moves to step S312. Then, the processor 33 changes the first threshold Z1 of the ultrasonic impedance to Z2 to set the same as a new threshold Z1, and changes the set time T1 to T2 to set the same as a new set time T1 (step S312). In the present modification, even before it is determined that the incision has been completed in the incision completion detection using the ultrasonic impedance value, the determination section 39 changes the gradual decrease definite threshold Z1 and the temporal threshold T1, which are parameters for detecting the incision completion, based on the temporal change in the high frequency impedance value. Then, the process moves to step S313.

In step S313, the determination section 39 determines whether the maximum value Zmax of the ultrasonic impedance is larger than the ultrasonic impedance Zt. When the maximum value Zmax is equal to or less than the ultrasonic impedance Zt (No), the processor 33 updates the maximum value Zmax of the ultrasonic impedance to the ultrasonic impedance Zt detected by the property detection section 37 (Zmax=Zt) (step S314). Then, the process returns to step S301. On the other hand, when it is determined that the maximum value Zmax is larger than the ultrasonic impedance Zt (Yes), the process moves to step S315. Then, the temporary peak holding section 51 of the processor 33 holds the maximum value Zmax as the temporary peak value of the ultrasonic impedance, and the processor 33 resets the count time T (T=0) (step S315).

After step S315, the determination section 39 of the processor 33 determines whether the high frequency impedance HZt is larger than the threshold HZ1 (step S316). When it is determined that the high frequency impedance HZt is equal to or less than the threshold HZ1. (No), the process moves to step S318. On the other hand, when it is determined that the high frequency impedance HZt is larger than the threshold HZ1 (Yes), the process moves to step S317. Then, the processor 33 changes the first threshold Z1 of the ultrasonic impedance to Z2 to set the same as a new threshold Z1, and changes the set time T1 to T2 to set the same as a new set time T1 (step S317). As described above, even before it is determined that the incision has been completed in the incision completion detection using the ultrasonic impedance value, the determination section 39 changes the gradual decrease definite threshold Z1 and the temporal threshold T1 based on the temporal change in the high frequency impedance value. Then, the process moves to step S318.

In step S318, the determination section 39 determines whether the gradually decreasing value Zmax−Zt of the ultrasonic impedance Zt from the maximum value Zmax of the ultrasonic impedance is larger than the threshold Z1 (first condition), and determines whether the count time T from the start of holding the maximum value Zmax is larger than the time T1 (second condition). When it is determined that the first condition and the second condition are not satisfied (No), the process returns to step S316.

On the other hand, when it is determined in step S318 that the first condition and the second condition are satisfied (Yes), the process moves to step S319. Then, the ultrasonic output control section 35 and the high frequency output control section 36 control output and the like (step S319). After step S319, the flow of treatment is terminated.

In the present modification, the same effect as described in the third exemplary embodiment can be obtained. In the present modification, when it is determined that the high frequency impedance HZt is larger than the threshold HZ1, the processor 33 changes the threshold Z1 and the time T1 that are determination parameters, and the determination section 39 of the processor 33 make the incision completion determination based on the temporal change in the electrical property value. Accordingly, the determination section 39 reliably determines that the treatment target has been completely cut and divided. Therefore, the energy treatment system capable of detecting the incision completion without erroneous detection is provided.

As described above, according to the respective exemplary embodiments and modifications of the present exemplary embodiments, in contrast to the conventional technique for determining that the treatment target has been cut and divided by detecting the peak of the ultrasonic impedance value and stopping the output, it is possible to prevent the incision remainder of the treatment target from being left by using the algorithm for determining the presence or absence of remaining treatment targets from the monitoring result of the high frequency impedance value when detecting the electrical property value including ultrasonic impedance, voltage, and power.

Although exemplary embodiments and modifications have been described above, the present exemplary embodiments are not limited to the above-described exemplary embodiments, and it is obvious to those skilled in the art that various improvements and modifications can be made without departing from the gist of the present invention. It is also obvious to those skilled in the art that the respective exemplary embodiments and the respective modifications can be appropriately combined. For example, the second exemplary embodiment and the third exemplary embodiment can be combined with the third modification or the fourth modification of the first exemplary embodiment.

Additional advantages and modifications will readily occur to those skilled in the art. Therefore, the exemplary embodiments are not limited to the specific details, and representative devices shown and described herein. Accordingly, various modifications may be made without departing from the spirit or scope of the general inventive concept as defined by the appended claims and their equivalents.

What is claimed is:

1. An energy treatment system comprising:
a first power supply;
a second power supply;
an ultrasonic transducer configured to generate ultrasonic vibration by electric power supplied from the first power supply;
a first gripping piece to which the ultrasonic vibration generated by the ultrasonic transducer is transferred, the first gripping piece being configured to perform treatment relating to a treatment target using the ultrasonic vibration, the first gripping piece having a probe electrode through which a high frequency current flows by electric power supplied from the second power supply;
a second gripping piece including a jaw electrode which causes the high frequency current to flow through the probe electrode via the treatment target by being supplied with electric power from the second power supply, the jaw electrode being opened and closed relative to the first gripping piece so as to grip the treatment target together with the first gripping piece; and
a processor configured to:

temporally detect an electrical property value relating to the ultrasonic transducer based on a detected output current and a detected output voltage of the first power supply;
store a temporary peak value of the electrical property value relating to the ultrasonic transducer;
calculate a high frequency-related calculation value between the probe electrode and the jaw electrode based on a detected output current and a detected high frequency output voltage of the second power supply;
compare the electrical property value relating to the ultrasonic transducer and the temporary peak value to determine whether the high frequency-related calculation value exceeds a predetermined threshold if a comparison result satisfies a predetermined condition; and
only when the electric property value relating to the ultrasonic transducer satisfies the predetermined condition and in response to determining that the high frequency-related calculation value is greater than the predetermined threshold, perform at least one of: (i) stopping and decreasing output from the first power supply, and (ii) outputting a notification indicating a determination result.

2. The energy treatment system according to claim 1, wherein in response to determining that the electric property value satisfies the predetermined condition and the high frequency-related calculation value is larger than the predetermined threshold, the processor is configured to perform at least one of (i) stopping or decreasing output from the second power supply, and (ii) notifying the determination result.

3. The energy treatment system according to claim 1, wherein the electrical property value is one of: an ultrasonic impedance that is an electric impedance value of the ultrasonic transducer, a voltage value applied to the ultrasonic transducer, and an electric power value supplied to the ultrasonic transducer.

4. The energy treatment system according to claim 1, wherein the predetermined condition is that the electrical property value starts to decrease and a predetermined time has elapsed since the electrical property value started to decrease.

5. The energy treatment system according to claim 1, wherein the processor is configured to:
calculate an integrated value of an amount of change in the electrical property value, and
compare the integrated value with a predetermined value to determine whether the predetermined condition is satisfied.

6. The energy treatment system according to claim 1, wherein the processor is configured to:
determine that the electrical property value starts to decrease and calculate an integrated value of an amount of change in the electrical property value after the electrical property value starts to decrease, and
determine that the predetermined condition is satisfied when the integrated value exceeds a predetermined value.

7. The energy treatment system according to claim 1, wherein the processor is configured to:
calculate a time change rate of the electrical property value, and
compare the time change rate with a predetermined value to determine whether the predetermined condition is satisfied.

8. The energy treatment system according to claim 1, wherein the processor is configured to:
calculate a time change rate of the electrical property value, and
determine that the predetermined condition is satisfied when the calculated time change rate of the electrical property value is larger than a predetermined value and a predetermined time has elapsed since the electrical property value started to decrease.

9. The energy treatment system according to claim 1, wherein in response to determining that the predetermined condition is satisfied and the high frequency-related calculation value does not exceed the predetermined threshold, the processor is configured to reset a parameter relating to the predetermined condition and determine whether the predetermined condition is satisfied.

10. The energy treatment system according to claim 1, wherein in response to determining that the predetermined condition is satisfied and the high frequency-related calculation value does not exceed the predetermined threshold, the processor is configured to decrease the output of the first power supply.

11. The energy treatment system according to claim 1, wherein:
the second power supply outputs high frequency power, and
the high frequency power that is output from the second power supply to the jaw electrode treats the treatment target.

12. The energy treatment system according to claim 1, wherein the processor is configured to decrease the output of the first power supply and increase the output of the second power supply.

13. The energy treatment system according to claim 1, further comprising:
a treatment device including the ultrasonic transducer, the first gripping piece, and the second gripping piece;
a controller including the processor; and
a memory provided on the treatment device or the controller, the memory storing a set value, wherein
when the treatment device is connected to the controller, the processor is configured to read a setting value stored in the memory and set the predetermined condition or the predetermined threshold.

14. The energy treatment system according to claim 1, further comprising an input apparatus configured to receive an instruction from a user, wherein:
the processor is configured to set the predetermined condition or the predetermined threshold based on the instruction input into the input apparatus.

15. The energy treatment system according to claim 1, further comprising an input apparatus configured to receive an instruction from a user, wherein
the processor is configured to switch a type of the predetermined operation or the presence or absence of the predetermined operation based on the instruction input into the input apparatus.

16. The energy treatment system according to claim 1, wherein the electrical property value relating to the ultrasonic transducer is an ultrasonic impedance.

17. The energy treatment system according to claim 16, wherein the processor compares the ultrasonic impedance with the temporary peak value as a first determination for determining a treatment status of the treatment target.

18. The energy treatment system according to claim 17, wherein the high frequency related calculation value is a high frequency impedance value, and the processor compares the high frequency impedance with the predetermined threshold in accordance with the first determination result as a second determination for determining a treatment status of the treatment target.

19. The energy treatment system according to claim 18, wherein the processor repeats detecting an electrical property value relating to the ultrasonic transducer if the high frequency impedance value is equal to or smaller than the predetermined threshold.

20. A controller configured to:
control a first power supply to output electric power to an ultrasonic transducer of a treatment device that generates ultrasonic vibration; and
control a second power supply to output electric power to a gripping piece of the treatment device,
the treatment device including a first gripping piece of the gripping piece, the first gripping piece having a probe electrode that a current flows through by electric power supplied from the second power supply, and the treatment device including a second gripping piece of the gripping piece, the second gripping piece being opened and closed relative to the first gripping piece so as to grip the treatment target,
the controller comprising:
a processor configured to:
continuously detect an electrical property value relating to the ultrasonic transducer over a predetermined period of time based on a detected output current and a detected output voltage of the first power supply;
determine and store a maximum value of the electrical property value relating to the ultrasonic transducer detected during the predetermined period of time;
detect a high frequency impedance value between the probe electrode and the jaw electrode based on a detected output current and a detected output voltage of the second power supply;
determine whether (i) a predetermined condition is satisfied, and (ii) the high frequency impedance value exceeds a predetermined threshold, by comparing the electrical property value relating to the ultrasonic transducer and the temporary peak value; and
in response to determining that the electric property value relating to the ultrasonic transducer satisfies the predetermined condition and the high frequency impedance value is greater than the predetermined threshold, perform at least one of: (i) stopping and (ii) decreasing output from the first power supply, and output a notification indicating a determination result.

21. A control method of an output from a first power supply and an output from a second power supply, the first power supply being configured to output electric power to an ultrasonic transducer of a treatment device, the ultrasonic transducer being configured to generate ultrasonic vibration by the electric power from the first power supply, the treatment device including a first gripping piece to which the ultrasonic vibration generated by the ultrasonic transducer is transferred, the first gripping piece being configured to perform treatment on a treatment target using the ultrasonic vibration, the first gripping piece having a probe electrode through which a current flows by electric power supplied from the second power supply, and a second gripping piece including a jaw electrode supplied with electric power from the second power supply, the jaw electrode being opened and closed relative to the first gripping piece so as to grip the treatment target together with the first gripping piece, the method comprising:
temporally detecting an electrical property value relating to the ultrasonic transducer based on a detected output current and a detected output voltage of the first power supply;
storing a temporary peak value of the electrical property value relating to the ultrasonic transducer;
detecting a value relating to a high frequency supply power between the probe electrode and the jaw electrode based on a detected output current and a detected output voltage of the second power supply;
comparing the electrical property value relating to the ultrasonic transducer and the temporary peak value to determine whether a predetermined condition is satisfied, and whether the calculated value relating to the high frequency supply power exceeds a predetermined threshold; and
in response to determining that the electric property value relating to the ultrasonic transducer satisfies the predetermined condition and the calculated value relating to the high frequency supply power is greater than the predetermined threshold, performing at least one of: (i) stopping and (ii) decreasing output from the first power supply, and outputting a notification indicating a determination result.

\* \* \* \* \*